United States Patent
Yamano et al.

(10) Patent No.: US 8,387,462 B2
(45) Date of Patent: Mar. 5, 2013

(54) METHOD AND APPARATUS FOR ULTRASONIC TESTING OF WELD ZONES

(75) Inventors: Masaki Yamano, Osaka (JP); Hiroyuki Okubo, Osaka (JP); Takumi Horikiri, Osaka (JP)

(73) Assignee: Sumitomo Metal Industries, Ltd., Osaka (JP)

( * ) Notice: Subject to any disclaimer, the term of this patent is extended or adjusted under 35 U.S.C. 154(b) by 71 days.

(21) Appl. No.: 13/129,835

(22) PCT Filed: Nov. 18, 2009

(86) PCT No.: PCT/JP2009/069537
§ 371 (c)(1),
(2), (4) Date: Jun. 16, 2011

(87) PCT Pub. No.: WO2010/058784

PCT Pub. Date: May 27, 2010

(65) Prior Publication Data
US 2011/0239770 A1  Oct. 6, 2011

(30) Foreign Application Priority Data
Nov. 19, 2008 (JP) .................................. 2008-296065

(51) Int. Cl.
*G01N 29/00* (2006.01)
(52) U.S. Cl. ................. 73/632; 73/600; 73/622; 73/626
(58) Field of Classification Search .................... 73/632, 73/602, 598, 600, 620, 622, 625–628
See application file for complete search history.

(56) References Cited

U.S. PATENT DOCUMENTS

| | | | | |
|---|---|---|---|---|
| 4,406,167 A | * | 9/1983 | Maeda ............................. | 73/622 |
| 4,627,289 A | * | 12/1986 | Fukuda et al. .................. | 73/622 |
| 5,085,082 A | * | 2/1992 | Cantor et al. ................... | 73/622 |
| 5,804,730 A | * | 9/1998 | Pfannenstiel et al. .......... | 73/622 |
| 7,762,136 B2 | * | 7/2010 | Ume et al. ....................... | 73/597 |
| 7,784,347 B2 | * | 8/2010 | Messer et al. ................... | 73/618 |
| 8,266,964 B2 | * | 9/2012 | Iizuka et al. .................... | 73/592 |

(Continued)

FOREIGN PATENT DOCUMENTS

| | | |
|---|---|---|
| JP | 01-114749 | 5/1989 |
| JP | 03-261858 | 11/1991 |

(Continued)

OTHER PUBLICATIONS

Masaki Yamano et al. "Dai Kankei . . . no Kaihatsu", Denki Gakkai Kinzoku Sangyo Kenkyukai Shiryo, Sep. 22, 2006, vol. MID-06, No. 12-17, pp. 15-18.

*Primary Examiner* — J M Saint Surin
(74) *Attorney, Agent, or Firm* — Clark & Brody

(57) ABSTRACT

Provided are an ultrasonic testing method and an ultrasonic testing apparatus capable of accurately detecting flaws present in a weld zone of a test object, such as a welded pipe, regardless of the position of the flaws. An ultrasonic testing apparatus 100 includes an ultrasonic probe 1 which is provided with n (n≧2) transducers 11 arranged along a direction orthogonal to the weld line of a weld zone P1 of a test object P and is arranged so as to face the weld zone, and transmission/reception control means 2 which selects m (n>m≧1) transducers from the n transducers, causes the selected transducers to transmit and receive ultrasonic waves to and from the weld zone, and switches the selected transducers one after another. The transmission/reception control means switches the selected transducers one after another so that the range of an effective beam width of each of the selected transducers that have been switched for a flaw to be detected has an overlapping portion, and in the transmission/reception control means, the flaw detection sensitivity is adjusted beforehand for each of the selected transducers so that maximum echo intensities from a flaw to be detected, which are each received by each of the selected transducers that have been switched, become substantially equal to each other.

11 Claims, 12 Drawing Sheets

FOREIGN PATENT DOCUMENTS

| | | |
|---|---|---|
| JP | 05-79829 | 3/1993 |
| JP | 09-229918 | 9/1997 |
| JP | 10-153587 | 6/1998 |
| JP | 2002-022714 | 1/2002 |
| JP | 2004-157113 | 6/2004 |
| JP | 3674131 | 7/2005 |
| JP | 2006-82135 | 3/2006 |
| JP | 2007-178147 | 7/2007 |

* cited by examiner

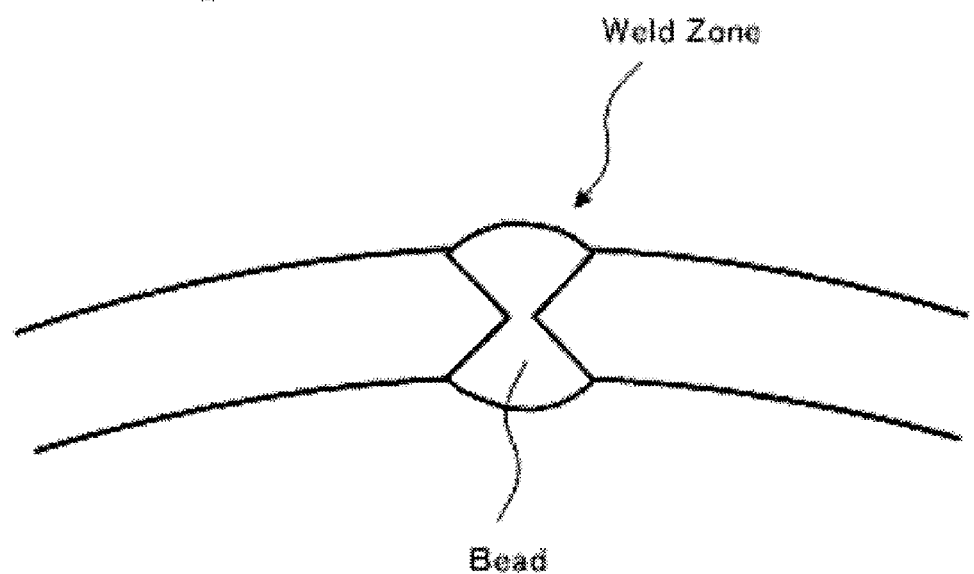

METHOD AND APPARATUS FOR ULTRASONIC TESTING OF WELD ZONES

TECHNICAL FIELD

The present invention relates to an ultrasonic testing method and an ultrasonic testing apparatus capable of accurately detecting flaws present in a weld zone of a test object, such as a welded pipe or tube, regardless of the positions of the flaws. Hereinafter, "pipe or tube" is referred to as pipe when deemed appropriate.

BACKGROUND ART

Depending on welding methods and welding conditions, various flaws occur in a weld zone of a test object, such as a welded pipe. These flaws cause a quality deterioration of the weld zone. For this reason, the nondestructive inspection of weld zones is carried out using X-rays and ultrasonic waves.

X-ray inspection can easily detect spot flaws, such as pinholes and slag inclusions, and has been used in many inspections. However, X-ray inspection has problems of low inspection efficiency, high equipment cost, and the like. For this reason, in submerged arc welded (SAW) steel pipe, ultrasonic testing is first performed and then X-ray inspection is performed only on opposite pipe ends and areas where it is determined by ultrasonic testing that there are flaws.

On the other hand, ultrasonic testing is suitable for detecting planar flaws, such as crack flaws and lack of fusion, and is superior to X-ray inspection in terms of inspection efficiency and equipment cost. Ultrasonic testing is therefore adopted to examine the whole weld zone except opposite pipe ends.

As an example of a conventional ultrasonic testing method for weld zones, an online automatic testing method in the manufacturing process of SAW steel pipe will be summarized below. In conventional ultrasonic testing of SAW steel pipe, as described in Non-Patent Literature 1 ("Ultrasonic Testing Method for Welded Pipe", Iron and Steel Institute of Japan, Feb. 22, 1999, pp. 60-62), a contrivance is made so that various types of flaws occurring in a weld zone can be detected without being overlooked. This contrivance is realized by arranging a plurality of ultrasonic probes for detecting longitudinal flaws (flaws extending in the direction of the weld line of a weld zone) and those for detecting transverse flaws (flaws orthogonal to the direction of the weld line of a weld zone) on each of the inner and outer surfaces of a pipe. Specifically, as shown in FIG. 1A, ultrasonic probes A1 and A2 for detecting longitudinal flaws on the inner surface of the pipe, ultrasonic probes B1 and B2 for detecting longitudinal flaws on the outer surface of the pipe, ultrasonic probes C1 and C2 for detecting transverse flaws on the inner surface of the pipe, and ultrasonic probes D1 and D2 for detecting transverse flaws on the outer surface of the pipe are arranged to perform ultrasonic testing.

By use of an eddy-current type or optical seam (weld line) detector and a seam tracking mechanism, the steel pipe is linearly transferred in the longitudinal direction while ensuring that the above-described plurality of ultrasonic probes can be constantly located in prescribed positions relative to a weld zone, whereby the whole weld zone is inspected.

However, ultrasonic testing by ultrasonic probes of general K-form arrangement as shown in FIG. 1A has a problem as described below. That is, for longitudinal flaws, it is possible to restrain the effects of the inclination of flaws from the radial direction of the steel pipe and the shape of flaws by performing ultrasonic testing from opposite sides, with a weld zone positioned therebetween. For transverse flaws, however, it is impossible to restrain the effects as described above because the ultrasonic testing of flaws on the inner and outer surfaces can be performed only in specific directions (the transfer direction of the steel pipe or the direction reverse to the transfer direction).

For this reason, in order to meet the requirements for inspection which have become increasingly severe in recent years, as shown in FIG. 1B, the trend is toward providing additional ultrasonic probes for detecting transverse flaws. Specifically, as shown in FIG. 1B, ultrasonic probes C3 and C4 for detecting transverse flaws on the inner surface of the pipe and ultrasonic probes D3 and D4 for detecting transverse flaws on the outer surface of the pipe are added. Incidentally, in the example shown in FIG. 1B, ultrasonic probes E1 and E2 for detecting longitudinal flaws are also added in order to increase the density of ultrasonic beams in the wall thickness direction of the pipe.

However, an increase in the number of ultrasonic probes to be arranged and the number of flaw detectors connected to each ultrasonic probe results in a steep rise in equipment cost. In addition, because it is necessary to set the distance between a weld zone and an ultrasonic probe, flaw detection sensitivity and the like for each ultrasonic probe, addition of ultrasonic probes poses a problem of long adjustment time, which is necessary until flaw detection becomes possible.

In the ultrasonic testing of transverse flaws by the ultrasonic probes of the arrangement shown in FIG. 1A and FIG. 1B, flaw detection is performed by using a pair of ultrasonic probes with a weld zone positioned therebetween (an ultrasonic echo transmitted by one ultrasonic probe is received by the other ultrasonic probe; for example, an ultrasonic echo transmitted by the ultrasonic probe C1 is received by the ultrasonic probe C2). For this reason, it is necessary to simultaneously adjust the positions of the pair of ultrasonic probes and testing conditions. It is difficult to simultaneously adjust the positions and the like of a pair of ultrasonic probes.

Furthermore, it is known that in the ultrasonic testing of transverse flaws by the ultrasonic probes of the arrangements shown in FIG. 1A and FIG. 1B, untested regions in pipe end portions are wide.

A method for solving problems as described above has been proposed, for example, by the present inventors in Patent Literature 1 (JP2002-22714A). This method is intended for detecting transverse flaws by transmitting and receiving ultrasonic waves in the longitudinal direction of a weld zone (in the direction of a weld line) with the aid of an ultrasonic probe arranged just above the weld zone (hereinafter, referred to as an above-bead probe).

However, in the angle-beam ultrasonic testing using this above-bead probe, the effective beam width relative to the bead width direction of a weld zone (in the direction orthogonal to a weld line) is narrow. For this reason, this technique has the problem that although it is possible to detect flaws present in the center of the bead width direction, flaws present at positions away from the center of the bead width direction tend to be overlooked, and hence the practical application of the angle-beam ultrasonic testing using this above-bead probe has not easily moved ahead.

The above-described "effective beam width" means the length of a range in which flaw echo intensity is not less than a prescribed intensity (for example, −3 dB when the maximum intensity is 0 dB) in the profile of the echo from a flaw (a flaw echo) which is obtained when an ultrasonic probe is scanned. In other words, so long as a flaw is present in this effective beam width, it is possible to detect the flaw in question at densities of not less than a prescribed intensity (for example, −3 dB) although the position of the flaw in question deviates from a position facing the center of the ultrasonic probe.

In the angle-beam ultrasonic testing using an above-bead probe, the narrow effective beam width relative to the bead width direction (an effective beam width obtained when an ultrasonic probe is scanned in the bead width direction) is caused by the beam shape of a weld zone. In other words, as illustrated as an example in FIG. 2, a bead (an excess weld metal) remains on the inner and outer surfaces of a weld zone and, therefore, it is difficult to simultaneously detect flaws present at positions different in the bead width direction of the weld zone.

FIGS. 3A to 3C show examples of the profile of flaw echo intensity obtained when an ultrasonic probe is scanned in the bead with direction of a weld zone. Specifically, FIGS. 3A and 3B show examples of the profile of echo intensity for a longitudinal hole B 1.6 mm in inside diameter worked in the center of the bead width direction of the weld zone (see FIG. 3C) and of longitudinal holes A and C 1.6 mm in inside diameter each worked at positions deviating±5 mm from the center of the bead width direction (see FIG. 3C). FIG. 3A shows an example of the profile in which the size of a transducer provided in the ultrasonic probe is 10×10 mm, and FIG. 3B shows an example of the profile in which the size of a transducer provided in the ultrasonic probe is 20×10 mm.

As shown in FIG. 3A, when the size of the transducer provided in the ultrasonic probe is 10×10 mm, the effective beam width (the length in the range of not less than −3 dB) for each of the longitudinal holes A to C is on the order of 4 mm. In this case, scanning positions of the ultrasonic probe (positions in the bead width direction) at which all of the longitudinal holes are capable of being detected, do not exist. From FIG. 3A it is apparent that, for example, when ultrasonic probes are arranged at the positions indicated by open arrows in FIG. 3A, compared to the echo intensity of the longitudinal hole B, the longitudinal hole C obtains an echo intensity of not more than −6 dB and the longitudinal hole A obtains an echo intensity of not more than −12 dB.

From FIG. 3A it is also apparent that a maximum value of echo intensity differs even when longitudinal holes have the same size.

On the other hand, as shown in FIG. 3B, when the size of the transducer provided in an ultrasonic probe is increased in the bead width direction to 20×10 mm, the effective beam width for each of the longitudinal holes A to C increases to the order of 15 mm. For this reason, the longitudinal holes B and C can be detected by arranging the ultrasonic probe at pre-scribed positions (for example, the positions indicated by open arrows in FIG. 3B). However, it is difficult to detect the longitudinal hole A because of the low echo intensity.

From FIG. 3B it is apparent that when the size of the transducer is increased, noises generated near the toe of a bead are amplified, resulting in a decrease in the S/N ratio of flaw signals. A concrete description will be given below. The areas near both ends of the abscissa of FIGS. 3A and 3B correspond to the positions of the bead toe. The echo intensity (noise caused by the shape of the bead toe) is on the order of −21 dB maximum in the areas near both ends of the abscissa of FIG. 3A, whereas in FIG. 3B, the eco intensity increases to the order of −13 dB maximum. From this it is apparent that the S/N ratio of flaw signals decreases.

As described above, after all, it is difficult for an ultrasonic probe provided with a single transducer to detect all flaws worked at different positions in the bead width direction. For this reason, it becomes necessary to use an ultrasonic probe provided with a plurality of transducers.

Examples of a technique for preventing flaws from being overlooked by using an ultrasonic probe in which a plurality of transducers are arranged include Patent Literature 2 (JP3674131B). In the technique described in Patent Literature 2, a plurality of transducers are arranged on a straight line, ultrasonic waves are transmitted and received by selecting a transducer group consisting of a given number of consecutive transducers from the plurality of transducers and a transducer group that has been selected is switched one after another. And this switching pitch is set to be equal to or smaller than the practical effective beam width of ultrasonic waves radiated from one selected transducer group.

Incidentally, the above-described "practical effective beam width" is defined as the width of a beam in which a level of 3 dB below a peak value of a sound field intensity in the middle part of an ultrasonic probe (paragraph 0005 of Patent Literature 2) can be assured.

However, the technique described in Patent Literature 2 has a problem as described below.

The profile of a flaw echo intensity obtained when an ultrasonic probe is scanned cannot be uniquely determined only from the profile of a sound field intensity, and the flaw shape in the scanning direction of the ultrasonic probe has a great influence.

FIG. 4 shows examples of the profile of flaw echo intensity obtained when the same ultrasonic probe is scanned in the axial direction of a steel pipe for axial flaws (flaws extending in the axial direction of the steel pipe) and circumferential flaws (flaws extending in the circumferential direction of the steel pipe) worked in the steel pipe.

Because in the above-described examples the same ultrasonic probe is used, the profile of sound field intensity is the same, but as shown in FIG. 4, when flaws differ, the profile of flaw echo intensity becomes different. For this reason, in the practical effective beam width derived from a profile of sound field intensity, it is impossible to correctly determine the above-described switching pitch and flaws might be overlooked.

SUMMARY OF INVENTION

The present invention was made in view of such problems with conventional techniques, and the object of the present invention is to provide an ultrasonic testing method and an ultrasonic testing apparatus which capable of accurately detecting flaws present in a weld zone of a test object, such as a welded pipe, regardless of the position of the flaws.

In order to solve the above-described object, the present invention provides an ultrasonic testing method for a weld zone, comprising: an arrangement step of arranging an ultrasonic probe so as to face a weld zone of a test object, the ultrasonic probe having n (n≧2) transducers arranged along a direction orthogonal to a weld line of the weld zone of the test object; and a flaw detection step of selecting m (n>m≧1) transducers from the n transducers, and causing the selected transducers to transmit ultrasonic waves to the weld zone and to receive an echo from the weld zone, thereby detecting flaws in the weld zone; and a scanning step of switching the selected transducers one after another, the weld zone being subjected to ultrasonic testing by alternately repeating the flaw detection step and the scanning step, wherein in the scanning step, the selected transducers are switched one after another so that the range of an effective beam width of each of the switched selected transducers for a flaw to be detected has an overlapping portion, and wherein in the flaw detection step, the weld zone is subjected to flaw detection with a flaw detection sensitivity, which is adjusted beforehand for each of the selected transducers, so that maximum echo intensities from a flaw to be detected, which are each received by each of the selected transducers that have been switched, become substantially equal to each other.

Incidentally, in the present invention, "an effective beam width of each of the selected transducers for a flaw to be detected" means the length of the range in which a flaw echo intensity becomes not less than a prescribed intensity (for example, −3 dB when the maximum intensity is 0 dB) in a profile of the intensity of a flaw to be detected which is obtained when each of the selected transducers is scanned in a direction orthogonal to a weld line of a weld zone.

In the present invention, "the range of an effective beam width" means the range in which a flaw echo intensity becomes not less than a prescribed intensity (for example, −3 dB when the maximum intensity is 0 dB) in a profile of the intensity of a flaw to be detected which is obtained when each of the selected transducers is scanned in a direction orthogonal to a weld line of a weld zone. For example, if it is assumed that the above-described profile of echo intensity is symmetric, with the center of each of the selected transducers as a reference (an origin), and that the effective beam width is 4 mm, then the range of ±2 mm along a direction orthogonal to a weld line of a weld zone becomes "the range of an effective beam width."

Furthermore, in the present invention, that "the range of an effective beam width has an overlapping portion" means that the range of an effective beam width has an overlapping portion as viewed from a direction of a weld line of a weld zone.

According to the present invention, in the scanning step, the selected transducers are switched one after another so that the range of an effective beam width of each of the switched selected transducers for a flaw to be detected has an overlapping portion. For this reason, even when a flaw to be detected is present at any position in a direction orthogonal to a weld line of a weld zone, the flaw to be detected in question is present within the range of an effective beam width of any of the selected transducers. Therefore, the echo intensity of the flaw to be detected in question becomes not less than a prescribed intensity (for example, −3 dB when the maximum value of the flaw echo intensity obtained by the selected transducer in question is 0 dB).

According to the present invention, in the flaw detection step, the weld zone is subjected to flaw detection with a flaw detection sensitivity (the amplification degree of echo intensity), which is adjusted beforehand for each of the selected transducers, so that maximum echo intensities from a flaw to be detected, which are each received by each of the selected transducers that has been switched, become substantially equal to each other. And as described above, the flaw to be detected in question is present within the range of an effective beam width of any of the selected transducers, with a flaw detection sensitivity adjusted so that the maximum echo intensities become substantially equal to each other. For this reason, even when the echo of a flaw to be detected is detected by any of the selected transducers, in other words, even when a flaw to be detected is present at any position in a direction orthogonal to the weld line of a weld zone, it is possible to obtain a flaw echo intensity which is not less than a prescribed intensity (for example, −3 dB when the maximum value of the flaw echo intensity obtained by an ultrasonic probe is 0 dB). Because it is possible to obtain a flaw echo intensity which is not less than a prescribed intensity, it is possible to accurately detect a flaw to be detected.

In the case where the above-described test object is a pipe and angle-beam testing which involves causing ultrasonic waves to be transmitted and received along the axial direction of the pipe (along the weld line of a weld zone) is performed, in general, the flaw echo intensity decreases in inverse proportion to the propagation distance of ultrasonic waves. For this reason, there is adopted a method for increasing flaw detection sensitivity with an increase in the propagation distance to detect flaws with a DAC curve drawn in accordance with JIS Z3060 or conversely, to make a threshold value for detecting flaws constant regardless of the propagation distance of ultrasonic waves.

However, in the angle-beam ultrasonic testing in which an ultrasonic probe is arranged so as to face a weld zone, the following situation occurs frequently. This situation is such that in spite of the double propagation distance of ultrasonic waves, the flaw echo intensity obtained in the outer surface flaw detection of what is called 1.0 skip (the outer surface flaw detection is performed at the point in time when ultrasonic waves entering a pipe first reach the outer surface of the pipe after the ultrasonic waves are reflected from the inner surface of the pipe) is higher than the flaw echo intensity obtained in the inner surface flaw detection of what is called 0.5 skip (the inner surface flaw detection is performed at the point in time when ultrasonic waves entering a pipe first reach the inner surface of the pipe).

This is caused by the bead (excess weld metal) shape on the inner and outer surfaces of a weld zone. That is, this is because ultrasonic waves tend to diffuse in the bead width direction due to bead shape when the ultrasonic waves enter a weld zone via a coupling medium such as water, whereas the ultrasonic waves which are reflected from the inner surface of a weld zone and propagate to the outer surface tend to converge in the bead width direction.

For this reason, in order to detect flaws on the inner and outer surfaces equally, in contrast to the case of the above-described DAC curve, it is preferred that a threshold value obtained during 1.0-skip inner surface flaw detection be raised in comparison with a threshold value obtained during 0.5-skip inner surface flaw detection. Or alternatively, it is preferred that the flaw detection sensitivity during 1.0-skip outer surface flaw detection be lowered in comparison with the flaw detection sensitivity during 0.5-skip inner surface flaw detection.

If the test object is a pipe or tube, preferably, in the flaw detection step, the weld zone is subjected to flaw detection with flaw detection sensitivities for a pipe or tube inner surface and a pipe or tube outer surface, which are adjusted beforehand for each of the selected transducers so that maximum echo intensities from a flaw to be detected on the pipe or tube inner surface, which are each received by each of the selected transducers that have been switched, become substantially equal to each other, so that maximum echo intensities from a flaw to be detected on the pipe or tube outer surface, which are each received by each of the selected transducers that have been switched, become substantially equal to each other, and so that the flaw detection sensitivity for the pipe or tube outer surface becomes lower than the flaw detection sensitivity for the pipe or tube inner surface (so that maximum echo intensities from a flaw to be detected on the pipe or tube inner surface and maximum echo intensities from a flaw to be detected on the pipe or tube outer surface become substantially equal to each other).

Preferably, in the arrangement step, the ultrasonic probe is attached to a probe holder capable of moving along the direction of a weld line of the weld zone on the test object and the probe holder is placed on the test object, whereby the ultrasonic probe is arranged so as to face the weld zone, and in the flaw detection step, the weld zone is subjected to flaw detection while the probe holder is caused to move relatively in the direction of the weld line of the weld zone with respect to the test object.

In these preferred methods, the probe holder may be moved along the direction of the weld line, with the test object fixed (at standstill), or conversely, the test object may be moved along the direction of the weld line, with the probe holder fixed (at standstill).

It is possible to subject the whole weld zone to ultrasonic testing by using these preferred methods.

Preferably, in the arrangement step, a pair of the ultrasonic probes is arranged so that ultrasonic waves transmitted from transducers provided in each of the ultrasonic probes enter substantially the same point of the weld zone as viewed from a direction orthogonal to the weld line of the weld zone and so that an echo reflected from the weld zone surface among ultrasonic waves transmitted from transducers provided in one of the ultrasonic probes can be received by transducers provided in the other ultrasonic probe.

And preferably, the ultrasonic testing method according to the present invention further comprises a coupling evaluation step wherein for the pair of ultrasonic probes, the flaw detection step and the scanning step are alternately repeated, whereby a series of ultrasonic testing actions of the weld zone in which all of the selected transducers are used one after another, are finished, and before a next series of ultrasonic testing actions are started, ultrasonic waves are transmitted from the transducers provided in one of the ultrasonic probes, an echo reflected from the weld zone surface among the ultrasonic waves transmitted from transducers provided in one of the ultrasonic probes is received by transducers of the other ultrasonic probe, and on the basis of the intensity of the echo, an acoustic coupling between the pair of ultrasonic probes and the test object is evaluated.

According to this preferred method, a pair of ultrasonic probes is arranged so that an echo reflected from the weld zone surface among ultrasonic waves transmitted from transducers provided in one of the ultrasonic probes can be received by transducers provided in the other ultrasonic probe. And according to the above-described preferred method, in the coupling evaluation step, ultrasonic waves are transmitted from the transducers provided in one of the ultrasonic probes, an echo reflected from the weld zone surface among the transmitted ultrasonic waves is received by transducers of the other ultrasonic probe, and the echo intensity is evaluated. On the basis of the magnitude of this echo intensity, it is possible to evaluate whether air bubbles are not included in the coupling medium interposed between the ultrasonic probe and the test object and whether ultrasonic waves enter the weld zone normally. That is, it is possible to evaluate an acoustic coupling between the ultrasonic probe and the test object.

If an abnormality occurs in the acoustic coupling (if the intensity of the echo reflected from the above-described weld zone surface is not more than a prescribed level), then for example, an alarm is issued, an adjustment is made so that the acoustic coupling becomes normal, and thereafter it is possible to take an action of re-inspection. Or alternatively, it is also possible to take an action to enhance flaw detection sensitivity according to the degree of a decrease in the intensity of the echo reflected from the above-described weld zone surface. At any rate, according to the above-described preferred method, it is possible to stabilize flaw detection accuracy.

In order to solve the above-described object, the present invention provides an ultrasonic testing apparatus for a weld zone, comprising: an ultrasonic probe which is provided with n ($n \geq 2$) transducers arranged along a direction orthogonal to a weld line of a weld zone of a test object and is arranged so as to face the weld zone; and transmission/reception control means which selects m ($n > m \geq 1$) transducers from the n transducers, causes the selected transducers to transmit ultrasonic waves to the weld zone and to receive an echo from the weld zone, and switches the selected transducers one after another, wherein the transmission/reception control means switches the selected transducers one after another so that the range of an effective beam width of each of the selected transducers that have been switched for a flaw to be detected has an overlapping portion, and wherein in the transmission/reception control means, a flaw detection sensitivity is adjusted beforehand for each of the selected transducers so that maximum echo intensities from a flaw to be detected, which are each received by each of the selected transducers that have been switched, become substantially equal to each other.

The n transducers which the ultrasonic probe comprises are not limited to the configuration in which the n transducers are arranged linearly along the direction orthogonal to the weld line of the weld zone. The n transducers may be arranged in a staggered manner along the direction orthogonal to the weld line of the weld zone.

If the test object is a pipe or tube, preferably, in the transmission/reception control means, flaw detection sensitivities for a pipe or tube inner surface and a pipe or tube outer surface are adjusted beforehand for each of the selected transducers, so that maximum echo intensities from a flaw to be detected on the pipe or tube inner surface, which are each received by each of the selected transducers that have been switched, become substantially equal to each other, so that maximum echo intensities from a flaw to be detected on the pipe or tube outer surface, which are each received by each of the selected transducers that have been switched, become substantially equal to each other, and so that the flaw detection sensitivity for the pipe or tube outer surface becomes lower than the flaw detection sensitivity for the pipe or tube inner surface.

Preferably, the ultrasonic testing apparatus according to the present invention further comprises a probe holder to which the ultrasonic probe is attached and which is capable of moving on the test object along the direction of the weld line of the weld zone.

Preferably, the probe holder includes a frame portion, a pair of first rolling portions attached to the frame portion in such a manner as to face portions of the test object other than the weld zone, and a pair of second rolling portions attached to the frame portion in such a manner as to face the weld zone of the test object.

Also, the pair of first rolling portions is arranged with the ultrasonic probe positioned therebetween along the direction orthogonal to the weld line of the weld zone, and each of the first rolling portions is provided with at least four first rollers capable of rolling in the direction of the weld line of the weld zone with the ultrasonic probe positioned between at least two of the first rollers and at least two of the first rollers along the direction of the weld line of the weld zone.

Further, the pair of second rolling portions is arranged with the ultrasonic probe positioned therebetween along the direction of the weld line of the weld zone, and each of the second rolling portions is provided with a second roller capable of rolling in the direction of the weld line of the weld zone, and the second roller is capable of moving in conjunction with the ultrasonic probe along a direction toward the weld zone with respect to the frame portion.

According to these preferred configurations, the probe holder includes a pair of first rolling portions. This pair of first rolling portions is attached to the frame portion in such a manner as to face portions of the test object other than the weld zone, and is arranged with the ultrasonic probe positioned therebetween along the direction orthogonal to the weld line of the weld zone. And each of the first rolling portions is provided with first rollers capable of rolling in the direction of the weld line of the weld zone. The above-described configurations enable the first rollers provided in each of the first rolling portion to roll on the areas except the weld zone of the test object. For this reason, the probe holder and hence the ultrasonic probe attached to the probe holder can move smoothly without being affected by the complex bead shape of the weld zone.

According to the above-described preferred configurations, at least four first rollers, which are provided in each of the first rolling portions, are arranged along the direction of the weld line of the weld zone with the ultrasonic probe positioned between at least two of the first rollers and at least two of the first rollers. In other words, a total of at least four first rollers (at least two first rollers in one of the first rolling portion and at least two first rollers in the other of the first rolling portion) are arranged on one side along the direction of the weld line with respect to the ultrasonic probe, and a total of at least four first rollers are also arranged on the other side. Accordingly, even if the first rollers arranged on one side protrude from the end portion of the test object, a total of at least four first rollers arranged on the other side still remain on the test object. For this reason, even if the first rollers arranged on one side are in a protruding condition, it is possible to maintain the orientation of the probe holder and hence the orientation of the ultrasonic probe. In other words, because it is possible to move the ultrasonic probe to the end portions of the test object, it is possible to make the untested regions of the end portions of the test object narrow.

Furthermore, according to the above-described preferred configurations, the probe holder includes a pair of second rolling portions. The pair of second rolling portions is attached to the frame portion in such a manner as to face the weld zone of the test object, and is arranged with the ultrasonic probe positioned therebetween along the direction of the weld line of the weld zone. And each of the second rolling portions is provided with a second roller capable of rolling in the direction of the weld line of the weld zone. This second roller is capable of moving in conjunction with the ultrasonic probe along a direction toward the weld zone with respect to the frame portion. With the above configurations, during the rolling of the second roller provided in the second rolling portion on the weld zone of the test object, the second roller moves in a direction toward the weld zone in response to changes in the bead shape (bead height) of the weld zone and also the ultrasonic probe moves in conjunction with the second roller in the direction toward the weld zone. For this reason, it is possible to keep the distance between the ultrasonic probe and the bead surface of the weld zone constant, enabling flaw detection accuracy to be stabilized.

Even when a first rolling portion having the following configuration is adopted in place of the first rolling portion of the above-described preferred configurations, the same operational advantages as those of the above-described preferred configurations are produced. That is, it is possible to adopt the configuration in which each of the first rolling portions is provided with a third roller capable of rolling in the direction of the weld line of the weld zone, which is arranged along the direction orthogonal to the weld line of the weld zone so as to face the ultrasonic probe, and a pair of fourth rollers capable of rolling in the direction of the weld line of the weld zone, which is arranged with the third roller positioned therebetween along the direction of the weld line of the weld zone.

In order to detect even flaws present at any position in the bead width direction of the weld zone, it is preferred that a coupling medium be supplied to a space between the whole weld zone including the bead toe and the ultrasonic probe without the generation of air bubbles and turbulent flows. For this purpose, a method which involves causing a coupling medium to flow is insufficient, and it is necessary to cause a coupling medium to accumulate in the above-described space by temporarily restraining the outflow of the coupling medium. Furthermore, it is necessary to cause a coupling medium to accumulate so that the ultrasonic testing is less affected by the complex bead shape of the weld zone.

For this reason, preferably, the probe holder includes a coupling medium reservoir part for causing a coupling medium to accumulate inside by surrounding a space between the ultrasonic probe and the weld zone. And preferably, the coupling medium reservoir part has a bellows structure capable of expanding and contracting freely along the direction toward the weld zone on a side opposed to the weld zone.

According to this preferred configuration, it is possible to cause a coupling medium to accumulate inside the coupling medium reservoir part surrounding a space between the ultrasonic probe and the weld zone, and what is more, because the coupling medium reservoir part having a bellows structure expands and contracts in such a manner as to adapt itself to the bead shape of the weld zone, the ultrasonic testing is less affected by the complex bead shape of the weld zone and it is possible to cause the coupling medium to accumulate in a stable manner. For this reason, it is possible to stabilize flaw detection accuracy.

According to the present invention, it is possible to accurately detect flaws present in a weld zone of a test object, such as a welded pipe, regardless of the positions of the flaws.

BRIEF DESCRIPTION OF THE DRAWINGS

FIG. 2 is a diagram showing an example of a sectional shape of a weld zone of a pipe.

DESCRIPTION OF EMBODIMENTS

Hereinafter, referring to the accompanying drawings, an embodiment of the present invention will be described by taking the case where the test object is a welded pipe as an example.

Figure 5:
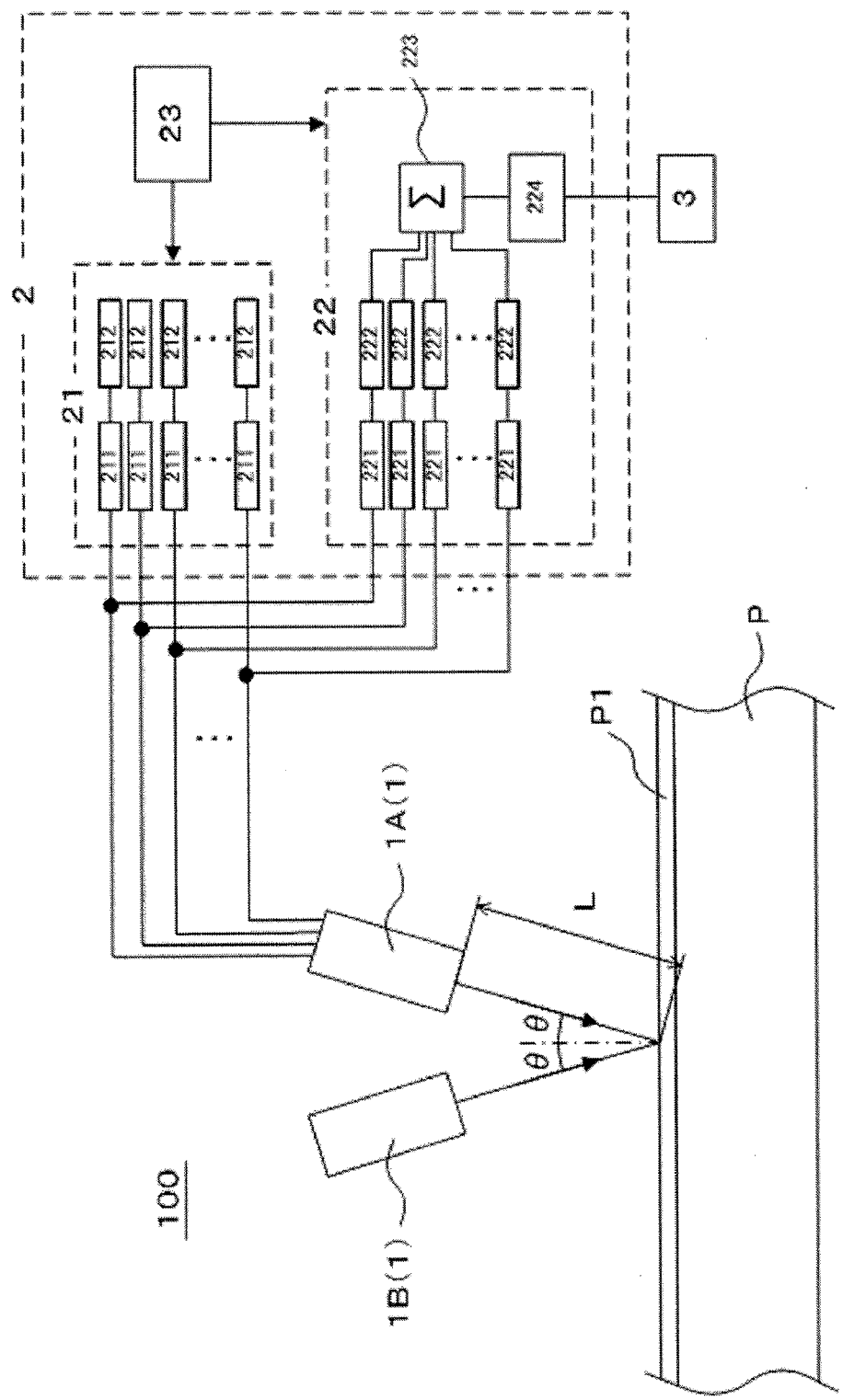
FIG. 5 is a front view showing the rough configuration of an ultrasonic testing apparatus for weld zones in an embodiment of the present invention.
Figure 6B:
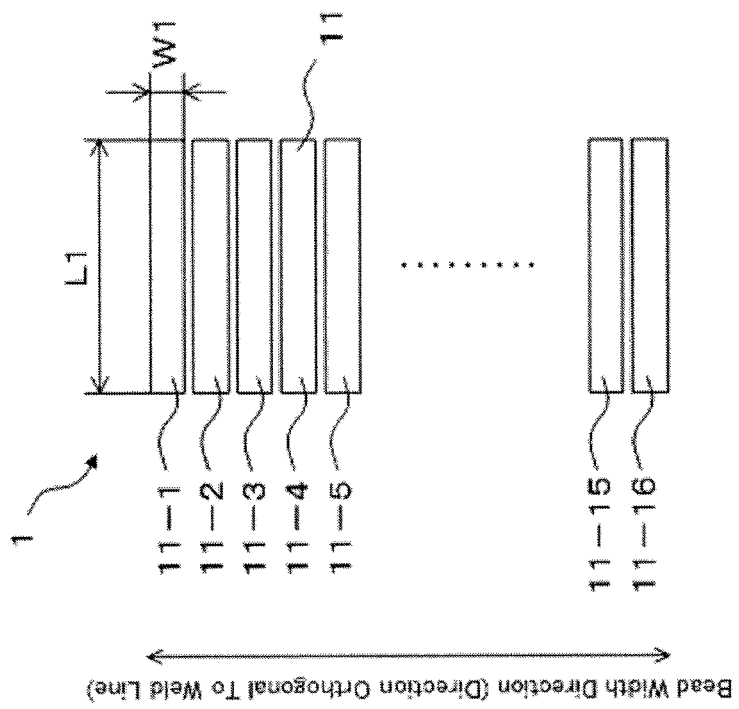
FIGS. 6A and 6B are diagrams showing the rough configuration of an ultrasonic probe shown in FIG. 5.
Figure 6A:
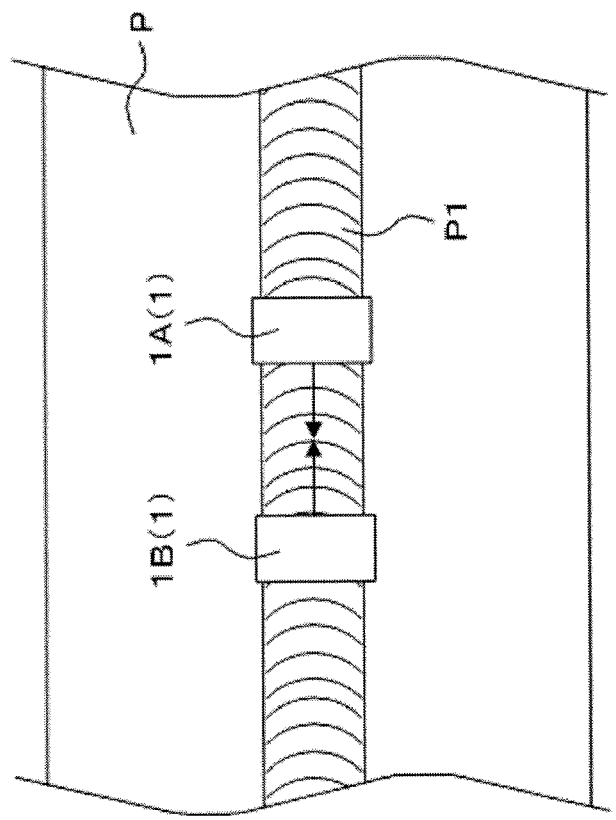
Figure 7C:
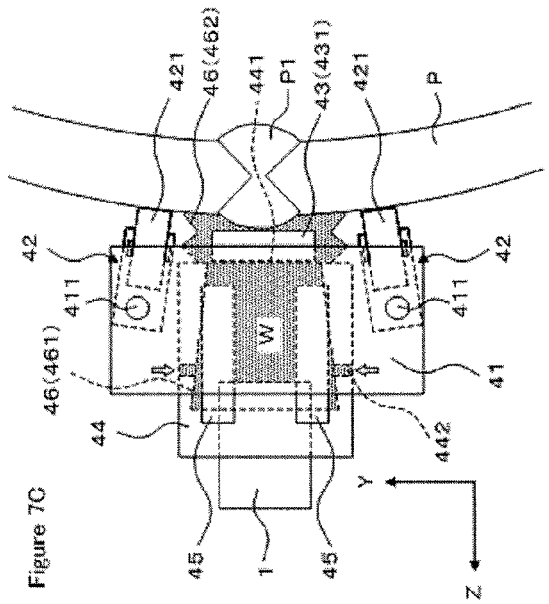
FIGS. 7A to 7C are diagrams showing the rough configuration of a probe holder to which the ultrasonic probe shown in FIG. 5 is attached.
Figure 7A:
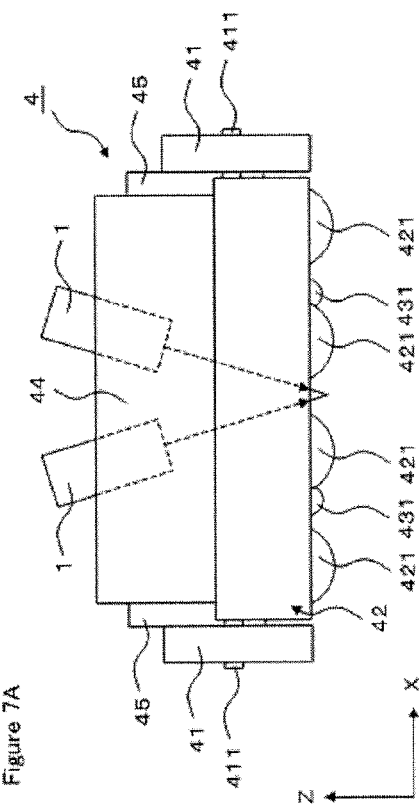
Figure 7B:
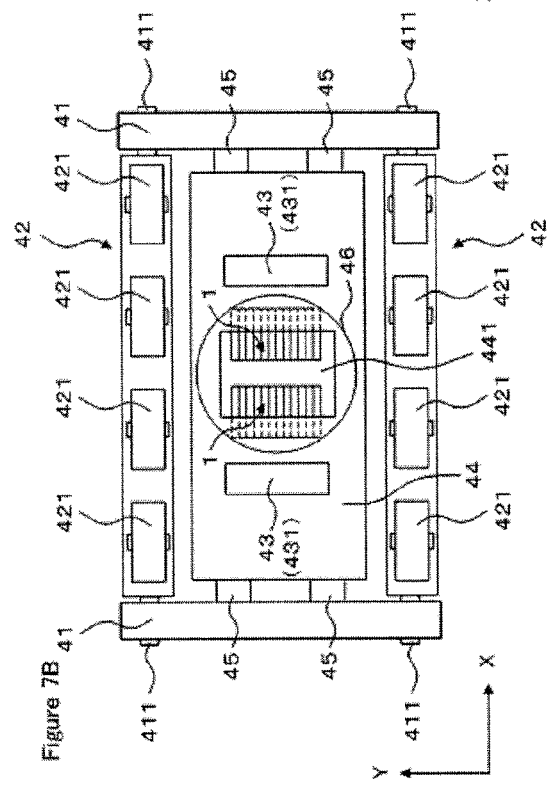

FIG. 5 is a front view showing the rough configuration of an ultrasonic testing apparatus for weld zones in an embodiment of the present invention. FIGS. 6A and 6B are diagrams showing the rough configuration of an ultrasonic probe shown in FIG. 5, FIG. 6A showing a plan view and FIG. 6B showing an enlarged plan view. FIGS. 7A to 7C are diagrams showing the rough configuration of a probe holder to which the ultrasonic probe shown in FIG. 5 is attached, FIG. 7A showing a front view, FIG. 7B showing a back view, and FIG. 7C a side view.

As shown in FIGS. 5 to 7, an ultrasonic testing apparatus 100 of this embodiment includes an ultrasonic probe 1 and transmission/reception control means 2. The ultrasonic probe 1 is provided with n (n≧2) transducers 11 arranged along a direction orthogonal to the weld line of a weld zone P1 of a steel pipe P and is arranged so as to face the weld zone P1. The transmission/reception control means 2 selects m (n>m≧1) transducers 11 from the n transducers 11 (a set of transducers composed of the selected m transducers 11 is called selected transducers 11S), causes the selected transducers 11S to transmit ultrasonic waves to the weld zone P1 and to receive an echo from the weld zone P1, and switches the selected transducers 11S one after another. The ultrasonic testing apparatus 100 of this embodiment includes a flaw determining section 3 which detects flaws present in the steel pipe P by comparing an output signal from the transmission/reception control means 2 with a prescribed threshold value. Furthermore, the ultrasonic testing apparatus 100 of this embodiment includes a probe holder 4 to which the ultrasonic probe 1 is attached and which is capable of moving on the steel pipe P along the weld line of the weld zone P1.

The ultrasonic testing apparatus 100 of this embodiment includes a pair of ultrasonic probes 1 (1A and 1B), which will be described later, as a preferred configuration for evaluating an acoustic coupling between the ultrasonic probe 1 and the steel pipe P. The pair of ultrasonic probes 1A and 1B is arranged substantially in the shape of the letter V so that ultrasonic waves transmitted from transducers 11 provided in each of the ultrasonic probes enter substantially the same point of the weld zone P1 as viewed from a direction orthogonal to the weld line of the weld zone P1 and so that an echo reflected from the weld zone P1 surface among ultrasonic waves transmitted from transducers 11 provided in one of the ultrasonic probes 1A can be received by transducers 11 provided in the other ultrasonic probe 1B Each of the ultrasonic probes 1 of this embodiment is spaced from a steel pipe P 40 mm in wall thickness by a distance L=70 mm from the steel pipe P. The reason for this will be described later. Furthermore, each of the ultrasonic probes 1 is arranged in the direction of the weld line in such a manner as to be inclined by θ=19° with respect to the normal line of the steel pipe P (so that the incident angle θ of ultrasonic waves approximately equals 19°, θ≅19°). As a result of this, ultrasonic shear waves with a refraction angle of 45° propagate along the direction of the weld line.

The reason why each of the ultrasonic probes 1 is spaced from the steel pipe P 40 mm by a distance L=70 mm is as follows.

When an ultrasonic shear wave with a refraction angle of 45° propagates in the steel pipe P having a 40 mm wall thickness, the 0.5-skip propagation distance (the propagation distance over which the ultrasonic wave entering the steel pipe P first reaches the inner surface of the steel pipe P, is reflected and returns to the incident point) is calculated as follows:

(40 mm/sin 45°)×2=113 mm

The time required by the ultrasonic shear wave to propagate over the above-described propagation distance is calculated as follows by dividing the above-described propagation distance by a propagation velocity of an ultrasonic shear wave in steel, which is 3.2 mm/μsec):

113/3.2=35.35 μsec

The 1.25-skip propagation distance becomes 2.5 times the 0.5-skip propagation distance. For this reason, the time t1 required by an ultrasonic shear wave to propagate over the 1.25-skip transfer distance is calculated as follows:

$t1=35.35\times2.5=88.4$ μsec

On the other hand, the propagation distance over which an ultrasonic wave transmitted form one ultrasonic probe 1 travels from an point in time when the ultrasonic wave is reflected from the surface of the steel pipe P to a point in time when the ultrasonic wave returns to the surface of the steel pipe P after reaching the other ultrasonic probe 1 and being reflected, is twice the above-described distance L and hence 2L.

If the coupling medium interposed between each of the ultrasonic probes 1 and the steel pipe P is water, the time t2 required by an ultrasonic wave to propagate over the above-described propagation distance is calculated as follows by dividing the above-described propagation distance by a propagation velocity of an ultrasonic wave in water, which is 1.5 mm/μsec.

$t2=2L/1.5$

If t2>t1, then an echo which is reflected from the other ultrasonic probe 1 and is received by one ultrasonic probe 1 (a shape echo) appears later in time than a flaw echo and, therefore, it is possible to distinguish the shape echo from a flaw echo. In other words, there is no possibility that flaw detection accuracy is reduced by the above-described shape echo.

For the reason described above, the distance L satisfying t2>t1 is set at 70 mm (L=70 mm).

Each of the ultrasonic probes 1 of this embodiment is provided with the same 16 rectangular transducers 11 (11-1 to 11-16) arranged linearly in a direction orthogonal to the weld line of the weld zone P1 (the bead width direction) (that is, in this embodiment n=16). Each of the transducers 11 of this embodiment has a length L1 of 10 mm and a width W1 of 0.9 mm and is arranged at intervals of 0.1 mm. That is, the arrangement pitch in a direction orthogonal to the weld line of each of the transducers 11 is 1.0 mm. Each of the ultrasonic probes 1 is arranged so that the transducers 11-8 and 11-9 face the center of the bead width direction of the weld zone P1.

The transmission/reception control means 2 of this embodiment includes a transmitting section 21, a receiving section 22 and a control section 23. In FIG. 5, for the sake of convenience, only the transmission/reception control means 2 connected to one ultrasonic probe 1A is shown. In actuality, however, a similar transmission/reception control means 2 is connected also to the other ultrasonic probe 1B.

The transmitting section 21 is provided with pulsars 211 and delay circuits 212. The pulsars 211 are each connected to each of the transducers 11 and supply to each of the transducers 11 a pulse signal for causing ultrasonic waves to be transmitted from each of the transducers 11. The delay circuits 212 set delay time (transmission delay time) of a pulse signal to be supplied from each of the pulsars 211 to each of the transducers 11.

The receiving section 22 is provided with receivers 221, delay circuits 222, a waveform synthesis circuit 223, and an amplifier 224. The receivers 221 are each connected to each of the transducers 11 and amplify echoes received by each of the transducers 11. The delay circuits 222 set the delay time (reception delay time) of echoes amplified in each of the receivers 221. The waveform synthesis circuit 223 synthesizes echoes for which delay time has been set in each of the delay circuits 222. The amplifier 224 amplifies echoes synthesized in the waveform synthesis circuit 223. The amplification degree (flaw detection sensitivity) of the amplifier 224 is adjusted beforehand for each of the selected transducers 11S so that as will be described later, maximum echo intensities from a test object which are received in each of the selected transducers 11S switched in the control section 23 become substantially equal to each other.

The control section 23 switches selected transducers 11S one after another which consist of m transducers 11 transmitting and receiving ultrasonic waves in the arranged n transducers 11. On this occasion, the control section 23 switches the selected transducers 11S one after another so that the range of the effective beam width of each of the selected transducers 11S that have been switched for a flaw to be detected has an overlapping portion.

The control section 23 operates in such a manner as to determine the delay time which is set in the delay circuits 212 or the delay circuits 222 for each of the transducers 11 constituting each of the selected transducers 11S. In this embodiment, in order to simultaneously transmit and receive ultrasonic waves by each of the transducers 11 constituting each of the selected transducers 11S, the same transmission delay time and reception delay time are set for each of the transducers 11.

Furthermore, the control section 23 operates in such a manner as to switch the amplification degree of the amplifier 224 (flaw detection sensitivity) for each of the selected transducers 11S. Specifically, the amplification degree of the amplifier 224 is configured to be capable of being switched. Also, the control section 23 outputs to the amplifier 224 a control signal for changing the amplification degree according to the selected transducers 11S that has been switched so that the amplification degree determined beforehand for each of the selected transducers 11S is obtained. As described above, this amplification degree for each of the selected transducers 11S is determined beforehand so that maximum echo intensities from a flaw to be detected, which are received in each of the selected transducers 11S that have been switched, become substantially equal to each other.

Figure 1B:
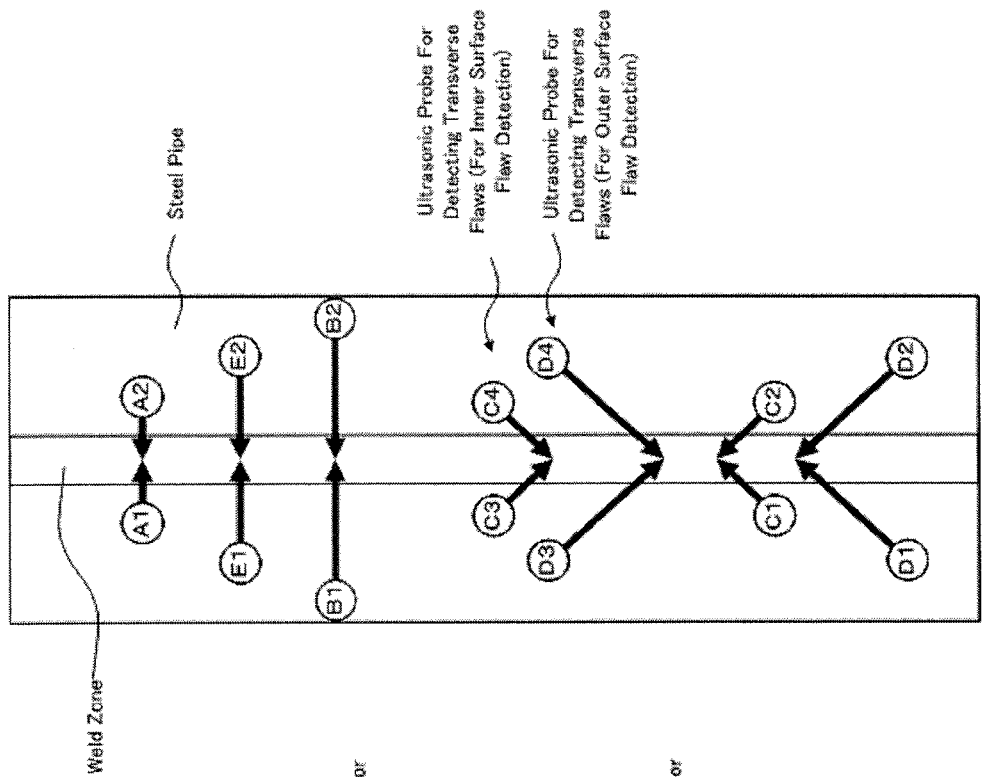
FIGS. 1A and 1B are explanatory diagrams to explain a conventional ultrasonic testing method for weld zones.
Figure 1A:
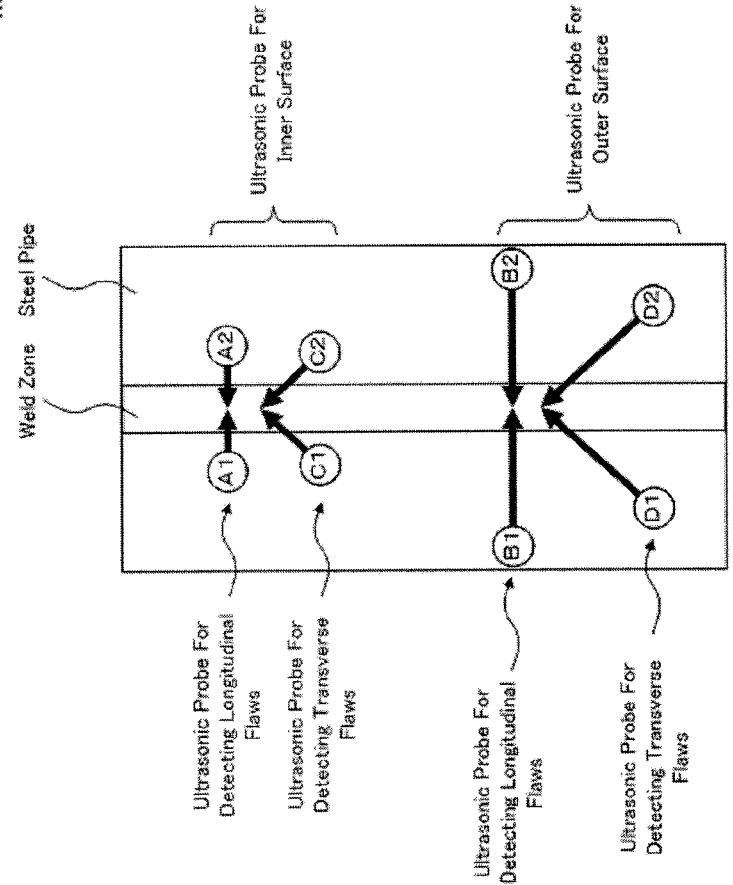
Figure 3B:
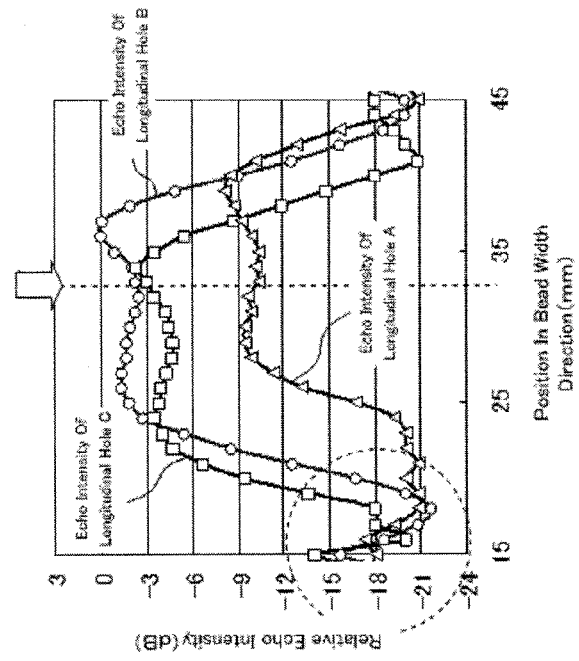
FIGS. 3A to 3C show examples of the profile of flaw echo intensity obtained when an ultrasonic probe is scanned in the bead width direction of a weld zone.

Because as described above, each of the ultrasonic probes 1 of this embodiment is provided with 16 transducers 11, it is possible to use selected transducers 11S consisting of any number of transducers 11 so long as the number of transducers 11 is not more than 15, and to simultaneously transmit and receive ultrasonic waves by each of the transducers 11 constituting each of the selected transducers 11S. However, if the opening width of each of the selected transducers 11S for the bead width direction of the weld zone P1 (=the number of the transducers 11 constituting the selected transducers 11S×the arrangement pitch of each of the transducers 11) is too large, as described above with reference to FIG. 3B, the S/N ratio of flaw signals decreases. Therefore, in this embodiment, each of the selected transducers 11S is composed of 10 consecutive transducers 11 (that is, in this embodiment m=10). In other words, the opening width of each of the selected transducers 11S in this embodiment is 10 mm (=10 pieces×1.0 mm).

Figure 3A:
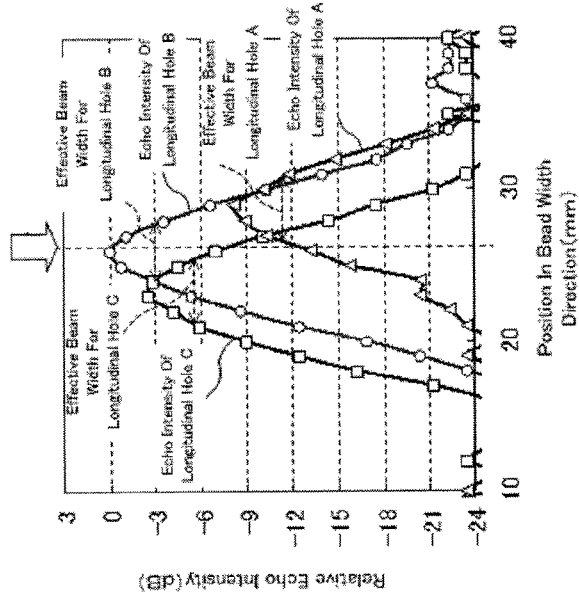

As described above, the opening width of each of the selected transducers 11S is 10 mm, and the length L1 of each of the transducers 11 constituting each of the selected transducers 11S is 10 mm (L1=10 mm). Therefore, as in the case where the size of the transducers is 10×10 mm described above with reference to FIG. 3A, the effective beam width of each of the selected transducers 11S in the bead width direction for a longitudinal hole having a 1.6 mm inside diameter worked in the weld zone P1 becomes approximately 4 mm. For this reason, in this embodiment, the pitch of switching of selected transducers 11S by the control section 23 is set at 3 mm so that the range of the effective beam width of each of the selected transducers 11S that have been switched for a flaw to be detected (a longitudinal hole having a 1.6 mm inside diameter) has an overlapping portion.

The ultrasonic testing which involves using the ultrasonic testing apparatus 100 of this embodiment is performed according to the following testing cycle while causing the ultrasonic probe 1 to move relatively with respect to the steel pipe P along the direction of the weld line of the weld zone P1. And the control section 23 of this embodiment switches the selected transducers 11S by shifting transducers 11 to be selected as in Steps 1 to 3 of the following testing cycle each by 3 transducers 11 at a time (that is, the switching pitch of the selected transducers 11S is 3 mm).

<Testing Cycle>

(1) Step 1: Ultrasonic testing is performed by use of the selected transducers 11S consisting of 10 transducers, which are transducers 11-1 to 11-10.

(2) Step 2: Ultrasonic testing is performed by use of the selected transducers 11S consisting of 10 transducers, which are transducers 11-4 to 11-13.

(3) Step 3: Ultrasonic testing is performed by use of the selected transducers 11S consisting of 10 transducers, which are transducers 11-7 to 11-16.

The ultrasonic testing of the whole steel pipe P is performed by repeating Steps 1 to 3 above.

As described above, the amplification degree of the amplifier 224 to be switched for each of the selected transducers 11S is specifically determined beforehand as follows. That is, the amplification degree of the amplifier 224 is determined so that the maximum echo intensity of the longitudinal hole C shown in FIG. 3C, which is obtained when ultrasonic waves are transmitted and received by the selected transducers 11S consisting of the transducers 11-1 to 11-10 switched in Step 1 above, becomes a prescribed intensity (for example, an 80% intensity on the CRT). And the amplification degree of the amplifier 224 is determined so that the maximum echo intensity of the longitudinal hole B shown in FIG. 3C, which is obtained when ultrasonic waves are transmitted and received by the selected transducers 11S consisting of the transducers 11-4 to 11-13 switched in Step 2 above, becomes an intensity substantially equivalent to the above-described intensity (for example, an 80% intensity on the CRT). Furthermore, the amplification degree of the amplifier 224 is determined so that the maximum echo intensity of the longitudinal hole A shown in FIG. 3C, which is obtained when ultrasonic waves are transmitted and received by the selected transducers 11S consisting of the transducers 11-7 to 11-16 switched in Step 3 above, becomes an intensity substantially equivalent to the above-described intensity (for example, an 80% intensity on the CRT). By doing as described above, the amplification degree of the amplifier 224 to be switched for each of the selected transducers 11S is determined beforehand. And the control section 23 also switches the amplification degree of the amplifier 224 according to the selected transducers 11S that have been switched so that this amplification degree becomes the amplification degree which is determined beforehand for each of the selected transducers 11S.

The ultrasonic testing apparatus 100 of this embodiment has the above-described configuration, and hence even when a flaw to be detected is present at any position in the direction orthogonal to the weld line of the weld zone P1, it is possible to obtain a flaw echo intensity of not less than a prescribed intensity (for example, −3 dB when a maximum value of the flaw echo intensity obtained by the ultrasonic probe 1 is 0 dB) and it is possible to accurately detect the flaw to be detected.

In this embodiment, as a preferred configuration, the amplification degree (flaw detection sensitivity) of the amplifier 224 for the inner surface of the steel pipe P and the outer surface of the steel pipe P is adjusted beforehand for each of the selected transducers 11S so that the following three conditions are satisfied. The first condition is that maximum echo intensities from a flaw to be detected on the inner surface of the steel pipe P, which are each received by each of the selected transducers 11S switched in the control section 23, are substantially equal to each other. The second condition is that maximum echo intensities from a flaw to be detected on the outer surface of the steel pipe P, which are each received by each of the selected transducers 11S switched in the control section 23, are substantially equal to each other. The third condition is that the amplification degree for the outer surface of the steel pipe P is lower than the amplification degree for the inner surface of the steel pipe P.

Specifically, in the amplifier 224, a flaw detection gate corresponding to 1.0-skip outer surface flaw detection and a flaw detection gate corresponding to 0.5-skip inner surface flaw detection are set. Also, the amplifier 224 is provided with amplifier circuits which correspond to each of the flaw detection gates and for each of which an independent amplification degree is set (an amplifier circuit for outer surface flaw detection and an amplifier circuit for inner surface flaw detection). And the amplifier 224 amplifies signals present in each of the flaw detection gate in the output signals of the waveform synthesis circuit 223 by use of each of the above-described amplifier circuits corresponding to each of the flaw detection gates.

As described above, the amplification degree of the amplifier circuit for inner surface flaw detection switched for each of the selected transducers 11S is determined beforehand so that maximum echo intensities of the inner surfaces of the longitudinal holes A to C obtained when ultrasonic waves are transmitted and received by each of the selected transducers 11S which are switched in Steps 1 to 3 become substantially equal to each other. And the control section 23 changes the amplification degree of the amplifier circuit for inner surface flaw detection according to the selected transducer 11S that has been switched. Similarly, the amplification degree of the amplifier circuit for outer surface flaw detection switched for each of the selected transducers 11S is determined beforehand so that maximum echo intensities of the outer surfaces of the longitudinal holes A to C obtained when ultrasonic waves are transmitted and received by each of the selected transducers 11S, which are switched in Steps 1 to 3, become substantially equal to each other. And the control section 23 changes the amplification degree of the amplifier circuit for outer surface flaw detection according to the selected transducer 11S that has been switched.

The amplification degree of the amplifier circuit for outer surface flaw detection is set at a value generally lower than the amplification degree of the amplifier circuit for inner surface flaw detection (for example, lower by the order of 3 to 10 dB) so that maximum echo intensities of the inner surfaces of the longitudinal holes A to C and maximum echo intensities of the outer surfaces thereof become substantially equal to each other. As a result of this, it is possible to use the same threshold value during outer surface flaw detection and inner surface flaw detection as the threshold value in the flaw determining section 3. And in the flaw determining section 3, it is possible to detect flaws on the inner and outer surfaces equally.

Also, in this embodiment, as a preferred configuration, an acoustic coupling between the ultrasonic probe 1 and the steel pipe P is evaluated when a series of ultrasonic testing actions (Steps 1 to 3 described above) of the weld zone P1 in which all of the selected transducers 11S are used one after another, have been finished and thereafter before a next series of ultrasonic testing actions are started. Specifically, ultrasonic waves are transmitted from the transducers 11-4 to 11-13 provided in one of the ultrasonic probes 1A, an echo reflected from the surface of the weld zone P1 among the transmitted ultrasonic waves is received by the transducers 11-4 to 11-13 provided in the other ultrasonic probes 1B, and the magnitude of intensity of the echo is evaluated. The above-described action is controlled by control means (not shown) which controls both the transmission/reception control means 2 connected to one ultrasonic probe 1A and the transmission/reception control means 2 connected to the other ultrasonic probe 1B. And an alarm is issued by the above-described control means if the intensity of the echo reflected from the weld zone P1 is not more than a prescribed level. This configuration enables an action of re-inspection to be taken after an adjustment is made so that the acoustic coupling becomes normal, and it is possible to stabilize flaw detection accuracy.

Although in this embodiment the configuration in which the ultrasonic probe 1 is provided with a plurality of the same transducers 11 arranged linearly in the bead width direction was described as an example, the present invention is not limited to this. For example, it is also possible to use an ultrasonic probe provided with a plurality of transducers having unequal widths 11A and 11B (the width of the transducer 11A and the width of the transducer 11B are different), which are arranged linearly in the bead width direction, as shown in FIG. 8A, and an ultrasonic probe provided with a plurality of transducers 11C, which are arranged in a staggered manner along the bead width direction, as shown in FIG. 8B.

Figure 8A:
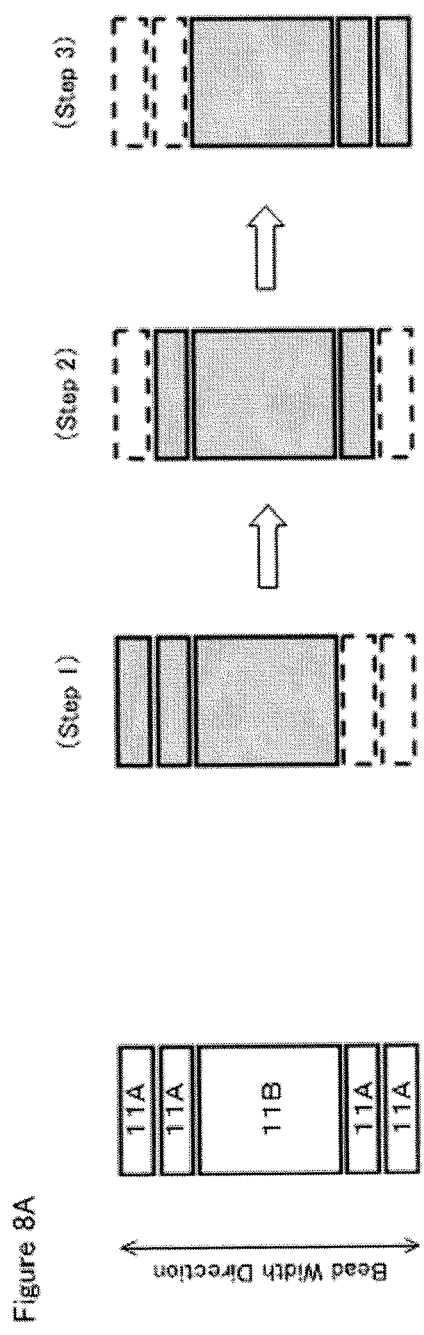
FIGS. 8A and 8B are diagrams showing examples of variation of a transducer provided in the ultrasonic probe shown in FIG. 6.
Figure 8B:
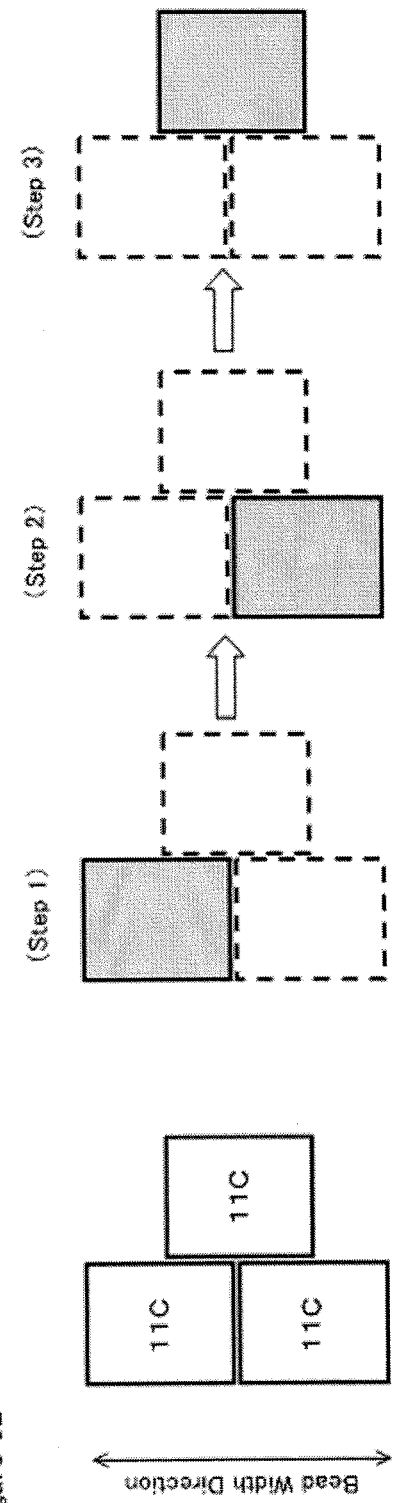

However, even in the case where the ultrasonic probes shown in FIGS. 8A and 8B are used, in the same manner as when the ultrasonic probe 1 of this embodiment is used, it is necessary to switch selected transducers one after another so that the range of the effective beam width of each of the selected transducers that have been switched (the hatched transducers in FIGS. 8A and 8B) has an overlapping portion. Also, in order to ensure that maximum echo intensities from a flaw to be detected, which are each received by each of the selected transducers that have been switched, become substantially equal to each other, it is necessary to adjust beforehand flaw detection sensitivity for each of the selected transducers.

A concrete configuration of the probe holder 4 provided in the ultrasonic testing apparatus 100 of this embodiment will be described below.

As shown in FIGS. 7A to 7C, the probe holder 4 of this embodiment includes a frame portion 41, a pair of first rolling portions 42, and a pair of second rolling portions 43. The pair of first rolling portions 42 is attached to the frame portion 41 in such a manner as to face portions of the steel pipe P other than the weld zone P1. The pair of second rolling portions 43 is attached to the frame portion 41 in such a manner as to face the weld zone P1 of the steel pipe P.

The pair of first rolling portions 42 is arranged with the ultrasonic probe 1 positioned therebetween along the direction orthogonal to the weld line of the weld zone P1 (the Y-direction of FIGS. 7B and 7C). Each of the first rolling portions 42 is attached to the frame portion 41 by use of a shaft member 411. And each of the first rolling portions 42 is provided with at least four first rollers 421 arranged with the ultrasonic probe 1 positioned between at least two of the first rollers and at least two of the first rollers (in this embodiment, two first rollers on each of the two sides with respect to the ultrasonic probe 1) along the direction of the weld line of the weld zone P1 (in the X-direction of FIGS. 7A and 7B). In this embodiment, radial bearings capable of rolling in the direction of the weld line of the weld zone P1 are used as the first rollers 421.

The pair of second rolling portions 43 is arranged with the ultrasonic probe 1 positioned therebetween along the direction of the weld line of the weld zone P1. Each of the second rolling portions 43 is provided with a second roller 431 capable of rolling in the direction of the weld line of the weld zone P1.

The second rollers 431 are capable of moving in conjunction with the ultrasonic probe 1 along a direction toward the weld zone P1 (the Z-direction of FIGS. 7A and 7C). Specifically, the ultrasonic probe 1 is mounted in a cabinet 44, and the second rollers 431 are attached to a lower face of the cabinet 44. And this cabinet 44 is attached to the frame portion 41 via a linear guide 45. This arrangement enables the cabinet 44 to move along the direction toward the weld zone P1 with respect to the frame portion 41, and hence also the second rollers 431 and the ultrasonic probe 1 are capable of moving in conjunction along the direction toward the weld zone P1.

The probe holder 4 of this embodiment includes, as a preferred configuration, a coupling medium reservoir part 46 for causing a coupling medium (in this embodiment, water) to accumulate inside by surrounding a space between the ultrasonic probe 1 and the weld zone P1. The coupling medium reservoir part 46 has a bellows structure capable of expanding and contracting freely along the direction toward the weld zone P1 on a side opposed to the weld zone P1.

Specifically, the coupling medium reservoir part 46 of this embodiment is provided with an inner wall portion 461 which extends from an opening 441 provided on the lower face of the cabinet 44 to the interior of the cabinet 44, and a bellows structure portion 462 attached to the lower face of the cabinet 44 in such a manner as to surround the opening 441. The space surrounded by the inner wall portion 461 (the interior of the cabinet 44) is in communication with the exterior of the cabinet 44 through a coupling medium supply path 442 provided inside the cabinet 44. The coupling medium W (the hatched portion in FIG. 7C) supplied from the outside of the cabinet 44 to the coupling medium supply path 442 flows into the space surrounded by the inner wall portion 461 and flows out of the opening 441 to outside the cabinet 44. On this occasion, since the space between the opening 441 and the weld zone P1 is surrounded by the bellows structure portion 462, the coupling medium W accumulates instead of flowing immediately.

According to the probe holder 4 of this embodiment having the configuration described above, the first rollers 421 provided in each of the first rolling portions 42 can roll on the portions other than the weld zone P1 of the steel pipe P. For this reason, the probe holder 4 and hence the ultrasonic probe 1 attached to the probe holder 4 can move smoothly without being affected by the complex bead shape of the weld zone P1.

Figure 9:
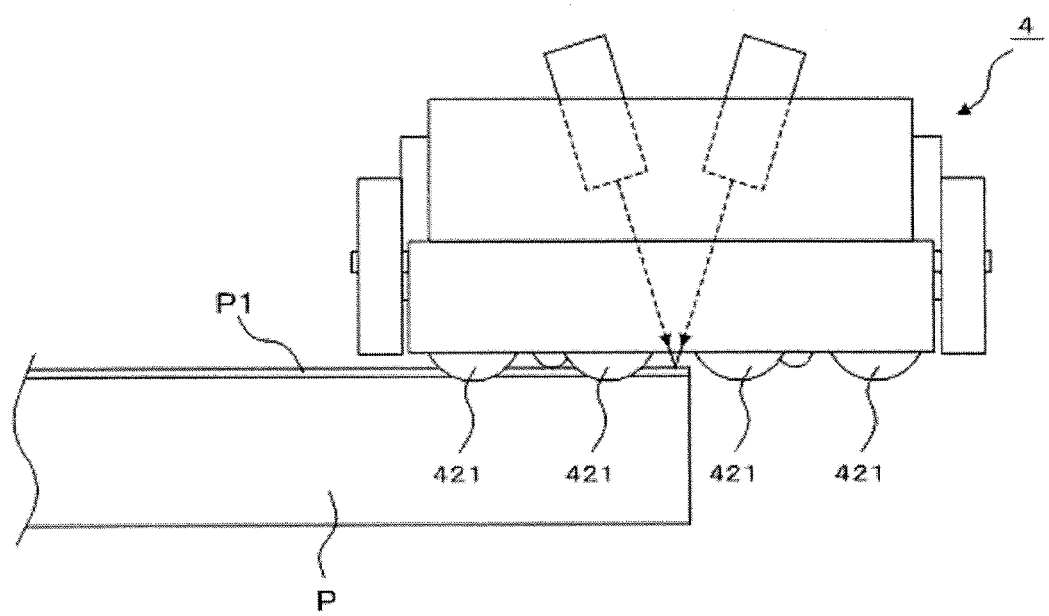
FIG. 9 is an explanatory diagram to explain the condition in which a pipe end is tested by using the ultrasonic probe attached to the probe holder shown in FIG. 7.

Also, according to the probe holder 4 of this embodiment, a total of four first rollers 421 are arranged on one side along the direction of the weld line of the weld zone P1 with respect to the ultrasonic probe 1, and a total of four first rollers 421 are arranged also on the other side. Accordingly, as shown in FIG. 9, even if the first rollers 421 arranged on one side protrude from the end portion of the steel pipe P, a total of four first rollers arranged on the other side still remain on the steel pipe P. For this reason, even if the first rollers 421 arranged on one side are in a protruding condition, it is possible to maintain the orientation of the probe holder 4 and hence the orientation of the ultrasonic probe 1. In other words, because it is possible to move the ultrasonic probe 1 to the end portions of the steel pipe P, it is possible to make the untested regions of the end portions of the steel pipe P narrow.

Figure 10A:
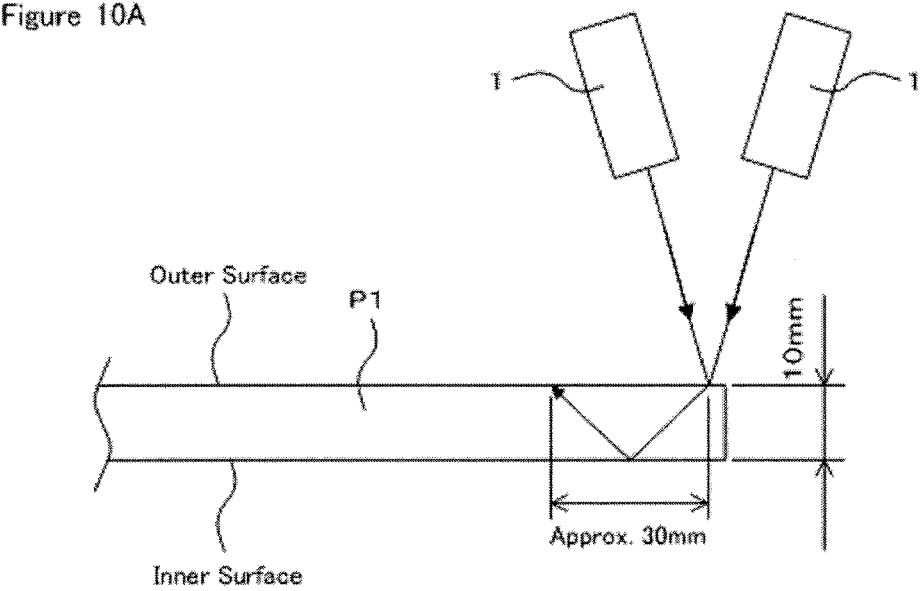
FIGS. 10A and 10B are diagrams to explain an untested region occurring when the ultrasonic testing apparatus of the present invention is used and an untested region occurring when a conventional ultrasonic testing apparatus is used, for comparison with each other.

More specifically, according to the probe holder 4 of this embodiment, flaw detection is possible even when the incident point of ultrasonic waves emitted from the ultrasonic probe 1 is in very close proximity to a pipe end of the steel pipe P. For this reason, when a wall thickness of the weld zone P1 is 10 mm as shown in FIG. 10A, it is possible to detect outer surface flaws present at positions of the order of 30 mm from a pipe end.

Figure 10B:
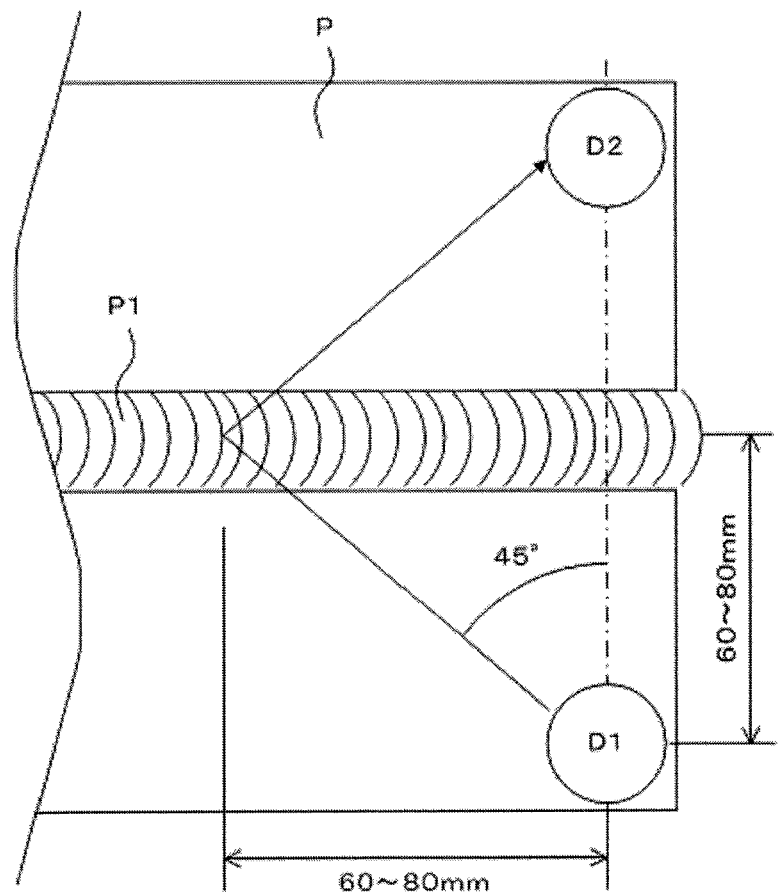

In contrast to this, in the ultrasonic testing using ultrasonic probes of the above-described general K-form arrangement as shown in FIG. 10B, it is necessary that ultrasonic probes D1 and D2 be arranged in such a manner as to face portions other than the weld zone P1 of the steel pipe P. And generally, the distance between the ultrasonic probes D1 and D2 and the center of the weld zone P1 becomes on the order of 60 mm to 80 mm. Furthermore, in the case of detection of transverse flaws, it is general practice to transmit ultrasonic waves from the ultrasonic probes D1 and D2 45° obliquely as viewed from the plane. For this reason, even when the ultrasonic probes D1 and D2 face the area in very close proximity to a pipe end of the steel pipe P, the incident point of ultrasonic waves becomes on the order of 60 mm to 80 mm from the pipe end and the region 60 mm to 80 mm or so away from the pipe end becomes an untested region. Furthermore, if the ultrasonic probes D1 and D2 are attached to a probe holder provided with four radial bearings, which has hitherto been used, it is impossible to cause the ultrasonic probes D1 and D2 to face the area in very close proximity to a pipe end of the steel pipe P and the above-described untested region expands further.

According to the probe holder 4 of this embodiment, during the rolling of the second rollers 431 provided in the second rolling portion 43 on the weld zone P1 of the steel pipe P, the second rollers 431 move in the direction toward the weld zone P1 in response to changes in the bead shape (bead height) of the weld zone P1. In association with this, the ultrasonic probe 1 moves in conjunction with the second rollers 431 in the direction toward the weld zone P1. For this reason, it is possible to keep the distance between the ultrasonic probe 1 and the bead surface of the weld zone P1 constant, enabling flaw detection accuracy to be stabilized.

Furthermore, according to the probe holder 4 of this embodiment, it is possible to cause a coupling medium to accumulate inside the coupling medium reservoir part 46 surrounding a space between the ultrasonic probe 1 and the weld zone P1, and what is more, because a bellows structure portion 462 of the coupling medium reservoir part 46 expands and contracts in such a manner as to adapt itself to the bead shape of the weld zone P1, the ultrasonic testing is less affected by the complex bead shape of the weld zone P1 and it is possible to cause the coupling medium to accumulate in a stable manner. For this reason, it is possible to stabilize flaw detection accuracy.

Figure 3C:
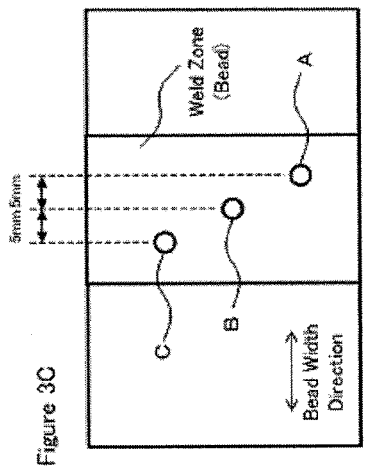
Figure 4:
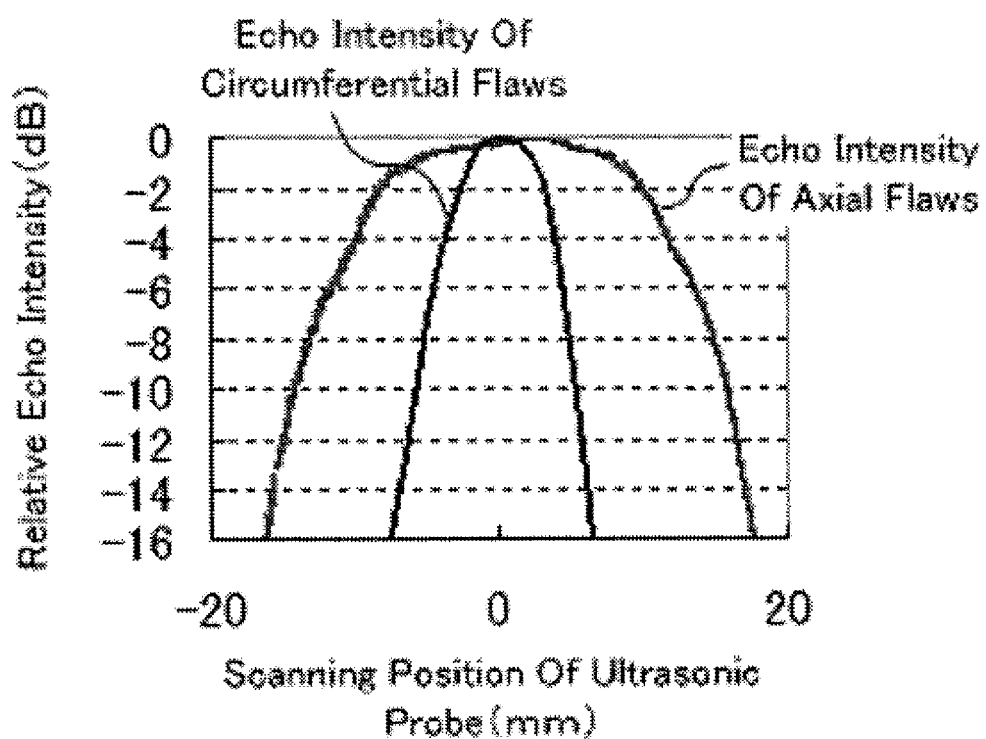
FIG. 4 shows examples of the profile of flaw echo intensity obtained when the same ultrasonic probe is scanned in the axial direction of a steel pipe for axial flaws and circumferential flaws which are worked in the steel pipe.
Figure 11:
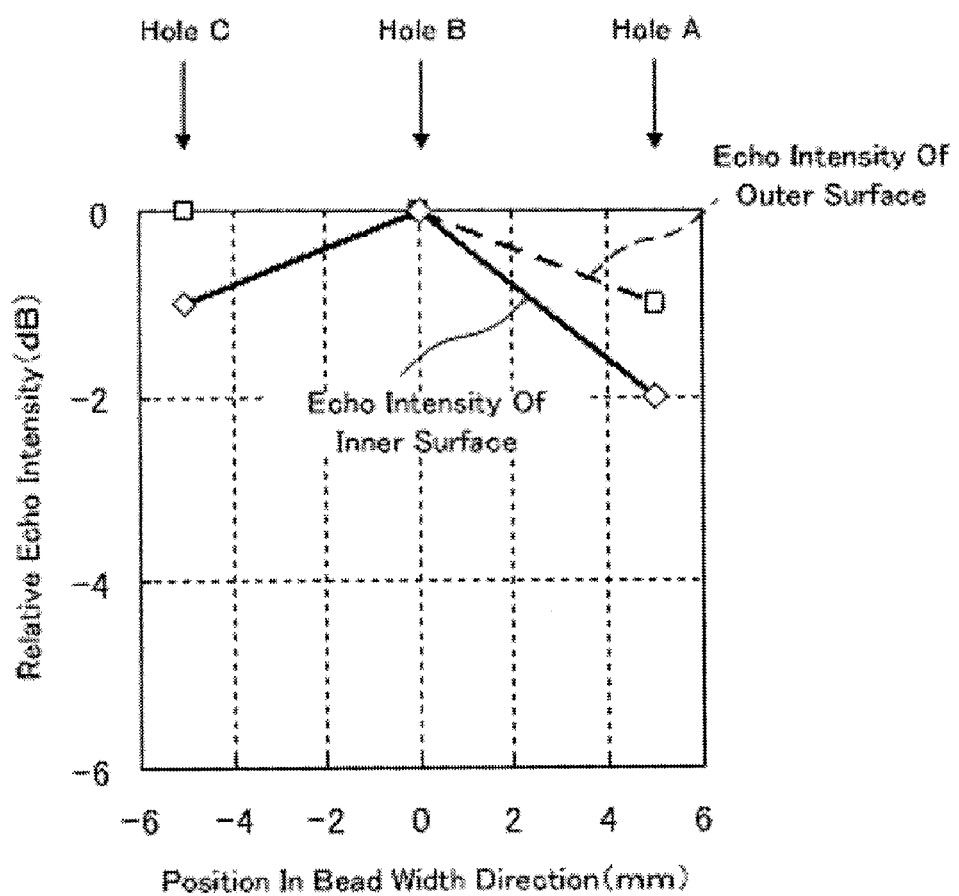
FIG. 11 is a graph showing an example of the result of ultrasonic testing conducted by using the ultrasonic testing apparatus of the present invention.

FIG. 11 is a graph showing the results of ultrasonic testing of the longitudinal holes A to C shown in FIG. 3C, which was conducted by use of the ultrasonic testing apparatus 100 having the configuration described above. The abscissa of FIG. 11 indicates the position in the bead width direction and the ordinate indicates a maximum echo intensity for each longitudinal hole outputted from the waveform synthesis circuit 223.

As is apparent from FIG. 11, according to the ultrasonic testing apparatus 100 of this embodiment, it is possible to accurately detect flaws on the inner and outer surfaces regardless of the positions of the flaws (positions in the bead width direction).

In this embodiment, the description was given of the configuration which is such that each of the first rolling portions 42 provided in the probe holder 4 is provided with at least four first rollers 421 arranged with the ultrasonic probe 1 positioned between at least two of the first rollers and at least two of the first rollers along the direction of the weld line of the weld zone P1. However, the present invention is not limited to this configuration, and it is also possible to adopt a probe holder 4A provided with first rolling portions 42A as shown in FIG. 12.

Figure 12:
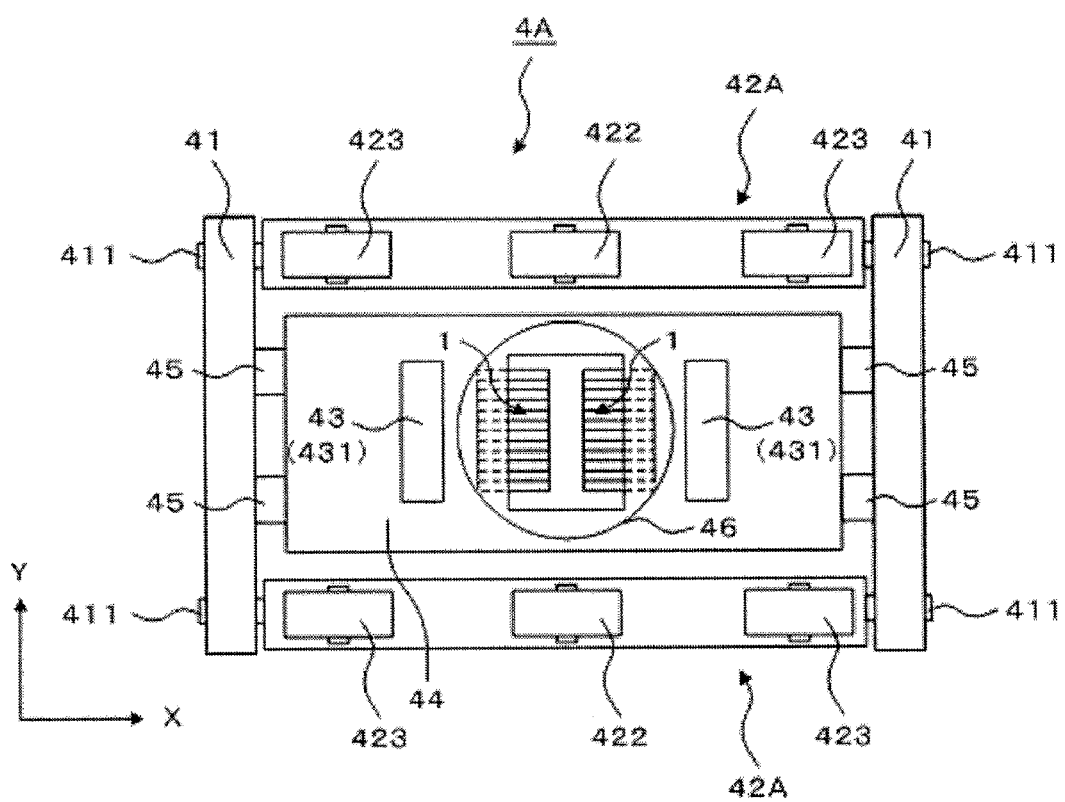
FIG. 12 is a back view showing the rough configuration of an example of variation of a probe holder to which the ultrasonic probe shown in FIG. 5 is attached.

FIG. 12 is a back view showing the rough configuration of an example of variation of a probe holder. As shown in FIG. 12, each of the first rolling portions 42A provided in the probe holder 4A of this example of variation is provided with a third roller 422 and a pair of fourth rollers 423. The third roller 422 is arranged along a direction orthogonal to the weld line of the weld zone P1 (the Y-direction of FIG. 12) in such a manner as to face the ultrasonic probe 1. The pair of fourth rollers 423 is arranged with the third roller 422 positioned therebetween along the direction of the weld line of the weld zone P1 (the X-direction of FIG. 12). In this example of variation, radial bearings capable of rolling in the direction of the weld line of the weld zone P1 are used as the third roller 422 and the fourth rollers 423.

According to the probe holder 4A of this example of variation, even if the two fourth rollers 423 arranged on one side with respect to the ultrasonic probe 1 along the direction of the weld line of the weld zone P1 protrude from the end portion of the steel pipe P, the two fourth rollers 423 arranged on the other side and two third rollers 422 (a total of four rollers) still remain on the steel pipe P. For this reason, even if the two fourth rollers 423 arranged on one side are in a protruding condition, it is possible to maintain the orientation of the probe holder 4A and hence the orientation of the ultrasonic probe 1. In other words, because it is possible to move the ultrasonic probe 1 to the end portions of the steel pipe P, it is possible to make the untested regions of the end portions of the steel pipe P narrow in the same manner as in the case where the above-described probe holder 4 is used.

The invention claimed is:

1. An ultrasonic testing method for a weld zone, comprising:
    an arrangement step of arranging an ultrasonic probe so as to face a weld zone of a test object, the ultrasonic probe having n (n≧2) transducers arranged along a direction orthogonal to a weld line of the weld zone of the test object; and
    a flaw detection step of selecting m (n>m≧1) transducers from the n transducers, and causing the selected transducers to transmit ultrasonic waves to the weld zone and to receive an echo from the weld zone, thereby detecting flaws in the weld zone; and
    a scanning step of switching the selected transducers one after another,
    the weld zone being subjected to ultrasonic testing by alternately repeating the flaw detection step and the scanning step,
    wherein in the scanning step, the selected transducers are switched one after another so that the range of an effective beam width of each of the switched selected transducers for a flaw to be detected has an overlapping portion, and
    wherein in the flaw detection step, the weld zone is subjected to flaw detection with a flaw detection sensitivity, which is adjusted beforehand for each of the selected transducers, so that maximum echo intensities from a flaw to be detected, which are each received by each of the selected transducers that have been switched, become substantially equal to each other.

2. The ultrasonic testing method for a weld zone according to claim 1,
    wherein the test object is a pipe or tube, and
    wherein in the flaw detection step, the weld zone is subjected to flaw detection with flaw detection sensitivities for a pipe or tube inner surface and a pipe or tube outer surface, which are adjusted beforehand for each of the selected transducers so that maximum echo intensities from a flaw to be detected on the pipe or tube inner surface, which are each received by each of the selected transducers that have been switched, become substantially equal to each other, so that maximum echo intensities from a flaw to be detected on the pipe or tube outer surface, which are each received by each of the selected transducers that have been switched, become substantially equal to each other, and so that the flaw detection sensitivity for the pipe or tube outer surface becomes lower than the flaw detection sensitivity for the pipe or tube inner surface.

3. The ultrasonic testing method for a weld zone according to claim 1,
    wherein in the arrangement step, the ultrasonic probe is attached to a probe holder capable of moving along the direction of a weld line of the weld zone on the test object and the probe holder is placed on the test object, whereby the ultrasonic probe is arranged so as to face the weld zone, and
    wherein in the flaw detection step, the weld zone is subjected to flaw detection while the probe holder is caused to move relatively in the direction of the weld line of the weld zone with respect to the test object.

4. The ultrasonic testing method for a weld zone according to claim 1, further comprising a coupling evaluation step;
    wherein in the arrangement step, a pair of the ultrasonic probes is arranged so that ultrasonic waves transmitted from transducers provided in each of the ultrasonic probes enter substantially the same point of the weld zone as viewed from a direction orthogonal to the weld line of the weld zone and so that an echo reflected from the weld zone surface among ultrasonic waves transmitted from transducers provided in one of the ultrasonic probes can be received by transducers provided in the other ultrasonic probe, and wherein in the coupling step, for the pair of ultrasonic probes, the flaw detection step and the scanning step are alternately repeated, whereby a series of ultrasonic testing actions of the weld zone in which all of the selected transducers are used one after another, are finished, and before a next series of ultrasonic testing actions are started, ultrasonic waves are transmitted from the transducers provided in one of the ultrasonic probes, an echo reflected from the weld zone surface among the ultrasonic waves transmitted from transducers provided in one of the ultrasonic probes is received by transducers of the other ultrasonic probe, and on the basis of the intensity of the echo, an acoustic coupling between the pair of ultrasonic probes and the test object is evaluated.

5. An ultrasonic testing apparatus for a weld zone, comprising:

an ultrasonic probe which is provided with n (n 2) transducers arranged along a direction orthogonal to a weld line of a weld zone of a test object and is arranged so as to face the weld zone; and transmission/reception control means which selects m (n>m≧1) transducers from the n transducers, causes the selected transducers to transmit ultrasonic waves to the weld zone and to receive an echo from the weld zone, and switches the selected transducers one after another, wherein the transmission/reception control means switches the selected transducers one after another so that the range of an effective beam width of each of the selected transducers that have been switched for a flaw to be detected has an overlapping portion, and wherein in the transmission/reception control means, a flaw detection sensitivity is adjusted beforehand for each of the selected transducers so that maximum echo intensities from a flaw to be detected, which are each received by each of the selected transducers that have been switched, become substantially equal to each other.

6. The ultrasonic testing apparatus for a weld zone according to claim 5, wherein the n transducers are arranged in a staggered manner along the direction orthogonal to the weld line of the weld zone.

7. The ultrasonic testing apparatus for a weld zone according to claim 5, wherein the test object is a pipe or tube, and wherein in the transmission/reception control means, flaw detection sensitivities for a pipe or tube inner surface and a pipe or tube outer surface are adjusted beforehand for each of the selected transducers, so that maximum echo intensities from a flaw to be detected on the pipe or tube inner surface, which are each received by each of the selected transducers that have been switched, become substantially equal to each other, so that maximum echo intensities from a flaw to be detected on the pipe or tube outer surface, which are each received by each of the selected transducers that have been switched, become substantially equal to each other, and so that the flaw detection sensitivity for the pipe or tube outer surface becomes lower than the flaw detection sensitivity for the pipe or tube inner surface.

8. The ultrasonic testing apparatus for a weld zone according to claim 5, further comprising:

a probe holder to which the ultrasonic probe is attached and which is capable of moving on the test object along the direction of the weld line of the weld zone.

9. The ultrasonic testing apparatus for a weld zone according to claim 8, wherein the probe holder includes a frame portion, a pair of first rolling portions attached to the frame portion in such a manner as to face portions of the test object other than the weld zone, and a pair of second rolling portions attached to the frame portion in such a manner as to face the weld zone of the test object, wherein the pair of first rolling portions is arranged with the ultrasonic probe positioned therebetween along the direction orthogonal to the weld line of the weld zone, wherein each of the first rolling portions is provided with at least four first rollers capable of rolling in the direction of the weld line of the weld zone with the ultrasonic probe positioned between at least two of the first rollers and at least two of the first rollers along the direction of the weld line of the weld zone, wherein the pair of second rolling portions is arranged with the ultrasonic probe positioned therebetween along the direction of the weld line of the weld zone, wherein each of the second rolling portions is provided with a second roller capable of rolling in the direction of the weld line of the weld zone, and wherein the second roller is capable of moving in conjunction with the ultrasonic probe along a direction toward the weld zone with respect to the frame portion.

10. The ultrasonic testing apparatus for a weld zone according to claim 8, wherein the probe holder includes a frame portion, a pair of first rolling portions attached to the frame portion in such a manner as to face portions of the test object other than the weld zone, and a pair of second rolling portions attached to the frame portion in such a manner as to face the weld zone of the test object, wherein the pair of first rolling portions is arranged with the ultrasonic probe positioned therebetween along the direction orthogonal to the weld line of the weld zone, wherein each of the first rolling portions is provided with a third roller capable of rolling in the direction of the weld line of the weld zone, which is arranged along the direction orthogonal to the weld line of the weld zone so as to face the ultrasonic probe, and a pair of fourth rollers capable of rolling in the direction of the weld line of the weld zone, which is arranged with the third roller positioned therebetween along the direction of the weld line of the weld zone, wherein the pair of second rolling portions is arranged with the ultrasonic probe positioned therebetween along the direction of the weld line of the weld zone, wherein each of the second rolling portions is provided with a second roller capable of rolling in the direction of the weld line of the weld zone, and wherein the second roller is capable of moving in conjunction with the ultrasonic probe along a direction toward the weld zone with respect to the frame portion.

11. The ultrasonic testing apparatus for a weld zone according to claim 8,
wherein the probe holder includes a coupling medium reservoir part for causing a coupling medium to accumulate inside by surrounding a space between the ultrasonic probe and the weld zone, and
wherein the coupling medium reservoir part has a bellows structure capable of expanding and contracting freely along the direction toward the weld zone on a side opposed to the weld zone.

* * * * *